US012710427B2

(12) United States Patent
Shih et al.

(10) Patent No.: US 12,710,427 B2
(45) Date of Patent: Aug. 18, 2026

(54) ANTI-HUMAN NEUROTENSIN RECEPTOR 1 ANTIBODY AND USE THEREOF

(71) Applicant: National Health Research Institutes, Miaoli County (TW)

(72) Inventors: Chuan Shih, Carmel, IN (US); Andrew Yueh, Miaoli County (TW); Ren-Huang Wu, Miaoli County (TW); Han-Shu Hu, Miaoli County (TW); Pei-Shan Wu, Miaoli County (TW); Zhi-Ping Yang, Miaoli County (TW); Yi-Yu Ke, Miaoli County (TW); Chiung-Tong Chen, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 766 days.

(21) Appl. No.: 17/926,452

(22) PCT Filed: Jun. 9, 2021

(86) PCT No.: PCT/US2021/036540

§ 371 (c)(1),
(2) Date: Nov. 18, 2022

(87) PCT Pub. No.: WO2021/252578

PCT Pub. Date: Dec. 16, 2021

(65) Prior Publication Data

US 2023/0183357 A1 Jun. 15, 2023

Related U.S. Application Data

(60) Provisional application No. 63/036,740, filed on Jun. 9, 2020.

(51) Int. Cl.

| | |
|---|---|
| ***G01N 33/575*** | (2026.01) |
| ***A61K 47/68*** | (2017.01) |
| ***A61P 35/00*** | (2006.01) |
| ***C07K 16/28*** | (2006.01) |
| *A61K 39/00* | (2006.01) |

(52) U.S. Cl.

CPC ... *G01N 33/5759* (2026.01); *A61K 47/68031* (2023.08); *A61K 47/6849* (2017.08); *A61P 35/00* (2018.01); *C07K 16/286* (2013.01); *A61K 2039/505* (2013.01); *C07K 2317/34* (2013.01); *C07K 2317/565* (2013.01); *C07K 2317/77* (2013.01); *C07K 2317/92* (2013.01); *G01N 2333/70571* (2013.01)

(58) Field of Classification Search

None

See application file for complete search history.

(56) References Cited

U.S. PATENT DOCUMENTS

| | | | | |
|---|---|---|---|---|
| 12,091,454 | B2 * | 9/2024 | Yu | C07K 16/2869 |
| 2005/0112678 | A1 | 5/2005 | Yang | |
| 2011/0223687 | A1 | 9/2011 | Nakamura et al. | |
| 2019/0010545 | A1 | 1/2019 | Deng et al. | |
| 2019/0153471 | A1 | 5/2019 | Paul et al. | |
| 2020/0025762 | A1 | 1/2020 | Edwards et al. | |

FOREIGN PATENT DOCUMENTS

| | | | |
|---|---|---|---|
| WO | 2010/069929 | A1 | 6/2010 |
| WO | 2020/041896 | A1 | 3/2020 |

OTHER PUBLICATIONS

Jiang et al, A Novel Peptide Isolated from a Phage Display Peptide Library with Trastuzumab Can Mimic Antigen Epitope of HER-2, the Journal of Biological Chemistry vol. 280, No. 6, Issue of Feb. 11, pp. 4656-4662, 2005.*

Mann et al, Epitope-Guided Engineering of Monobody Binders for in Vivo Inhibition of Erk-2 Signaling, ACS Chem. Biol. 2013, 8, 608-616.*

Nikolaou et al, The role of Neurotensin and its receptors in non-gastrointestinal cancers: a review, Cell Communication and Signaling, 2020, pp. 1-10.*

Dim, et al., "Novel Targeted siRNA-loaded Hybrid Nanoparticles: Preparation, Characterization and in vitro Evaluation," J. of Nanobiotechnology, 13(1):1-13, (2015).

Alomone Labs N, "Anti-Neurotensin Receptor 1 (extracellular) Antibody," dated Jan. 1, 2012. Retrieved from internet on Apr. 20, 2022 at https://www.alomone.com/p/anti-neurotemsin-receptor-1-extracellular/ANT-015.

* cited by examiner

*Primary Examiner* — Maria Marvich

(74) *Attorney, Agent, or Firm* — Morse, Barnes-Brown & Pendleton, P.C.; Lisa M. Warren, Esq.; Jeannie Wu

(57) ABSTRACT

An isolated antibody, comprising: a heavy chain variable domain ($V_H$) that is at least 75% identical to the amino acid sequence of SEQ ID NO: 1; and a light chain variable domain ($V_L$) that is at least 75% identical to the amino acid sequence of SEQ ID NO: 2; wherein the antibody binds specifically to human neurotensin receptor 1 (hNTSR1).

21 Claims, 13 Drawing Sheets

Specification includes a Sequence Listing.

FIG. 1
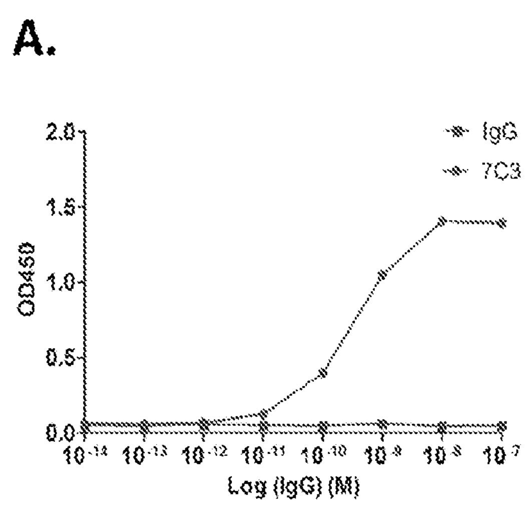
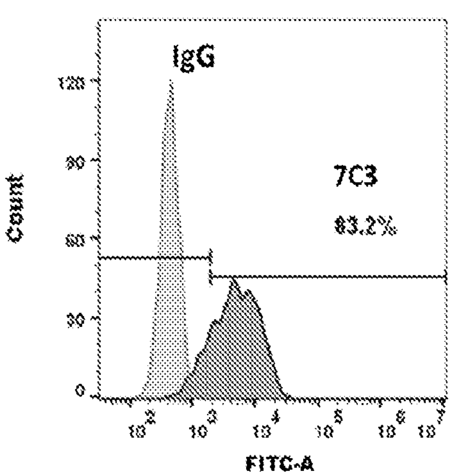
FIG. 2
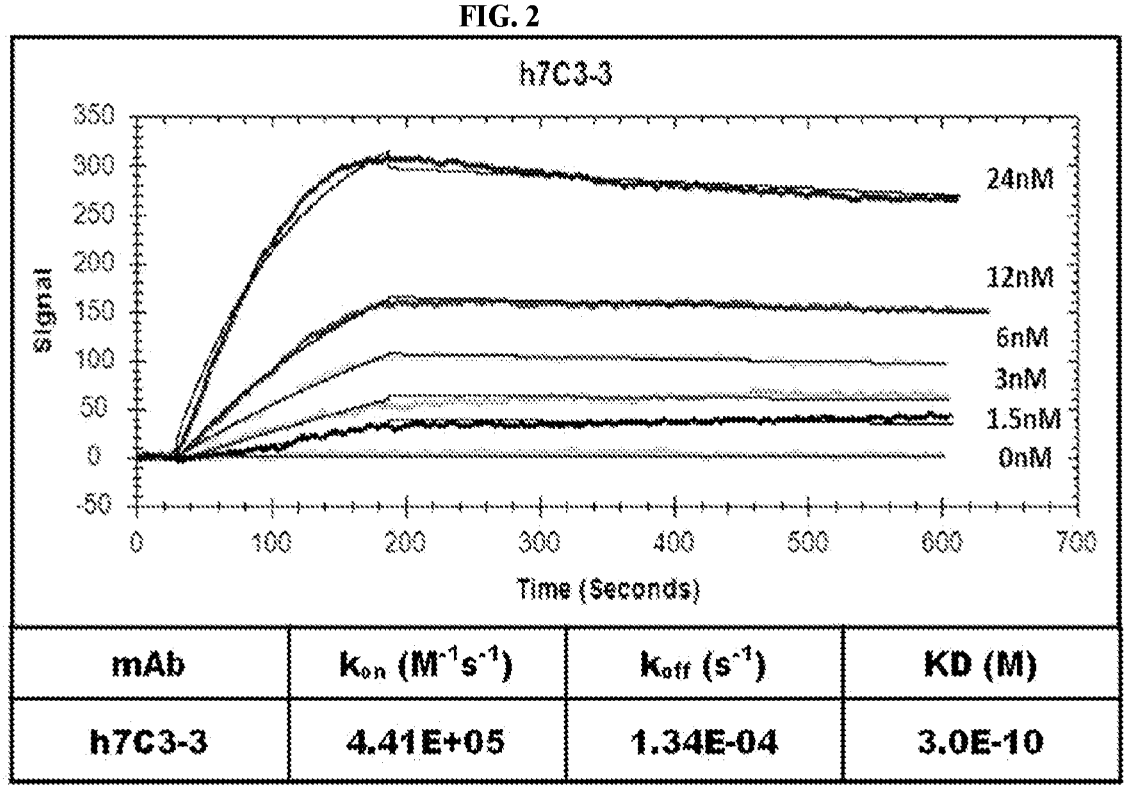
| mAb | $k_{on}$ ($M^{-1}s^{-1}$) | $k_{off}$ ($s^{-1}$) | KD (M) |
|---|---|---|---|
| h7C3-3 | 4.41E+05 | 1.34E-04 | 3.0E-10 |

A.

| variant | VH 9 | VH 82 | VL 79 | pI | FACS binding (%) |
|---|---|---|---|---|---|
| h7C3-3 | S | D | K | 8.9 | 83 |
| h7C3-4 | T | E | T | 8.4 | 80 |

```
                                                  CDRH1
h7C3-4 QVQLQQPGTVLVRPGASVKLSCKASGYAFTSSWIHWAKQRPGQGLEWIGQ
h7C3-5 QVQLVQSGAEVKKPGASVKVSCKASGYAFTSSWIHWVRQAPGQRLEWMGQ

             CDRH2
h7C3-4 IRPNSGNTYYNEKFKVKATLTVDTSSSTAYVELSSLTSEDSAVYYCARYH
h7C3-5 IRPNSGNTYYNEKFKVRVTITRDTSASTAYMELSSLRSEDTAVYYCARYH

       CDRH3
h7C3-4 YGFDYWGQGTLVTVSS
h7C3-5 YGFDYWGQGTLVTVSS
```

B.

```
                                                  CDRL1
h7C3-4 DVLMTQTPLSLPVSLGDQASISCRSSQSIVHSNGNTYLEWYLQKPGQSPK
h7C3-5 DIVMTQTPLSLSVTPGQPASISCRSSQSIVHSNGNTYLEWYLQKPGQSPQ

          CDRL2                                     CDRL3
h7C3-4 LLIYKVSNRFSGVPDRFSGSGSGTDFTLTISRVEAEDLGVYYCFQGAHLP
h7C3-5 LLIYKVSNRFSGVPDRFSGSGSGTDFTLKISRVEAEDVGVYYCFQGAHLP

h7C3-4 WTFGGGTKLEIKR
h7C3-5 WTFGGGTKVEIKR
```

C.

| variant | FACS binding (%, 1 μg/ml) |
|---|---|
| h7C3-4 | 97.71±1.64 |
| h7C3-5 | 98.42±0.49 |

FIG. 8
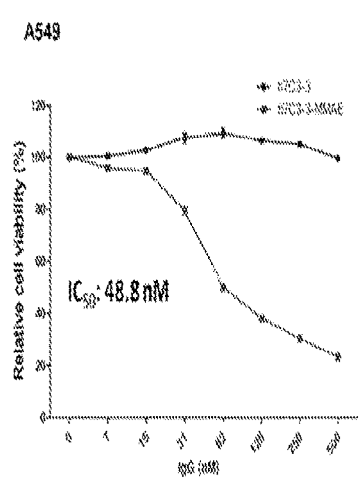
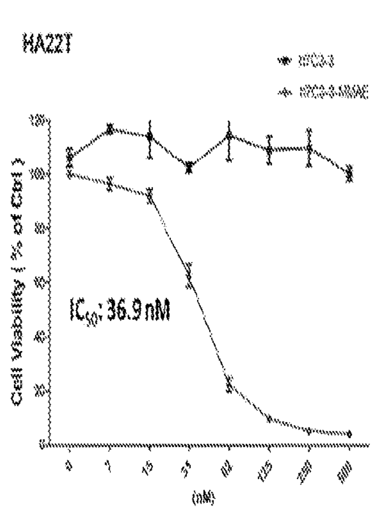
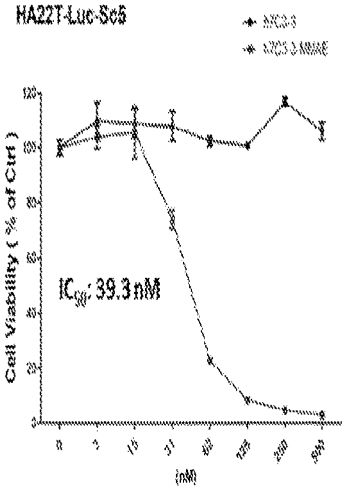
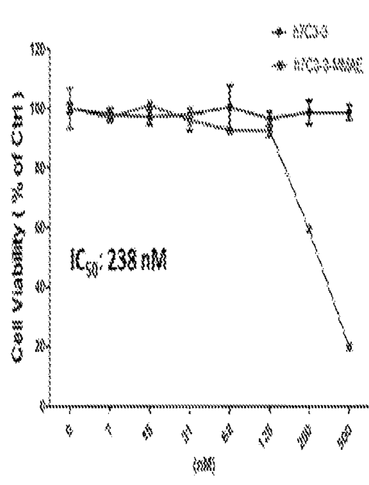
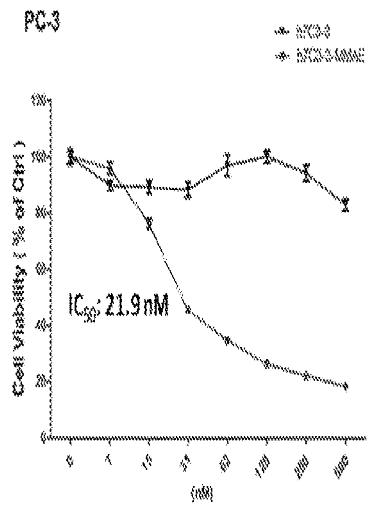

Figure 11:
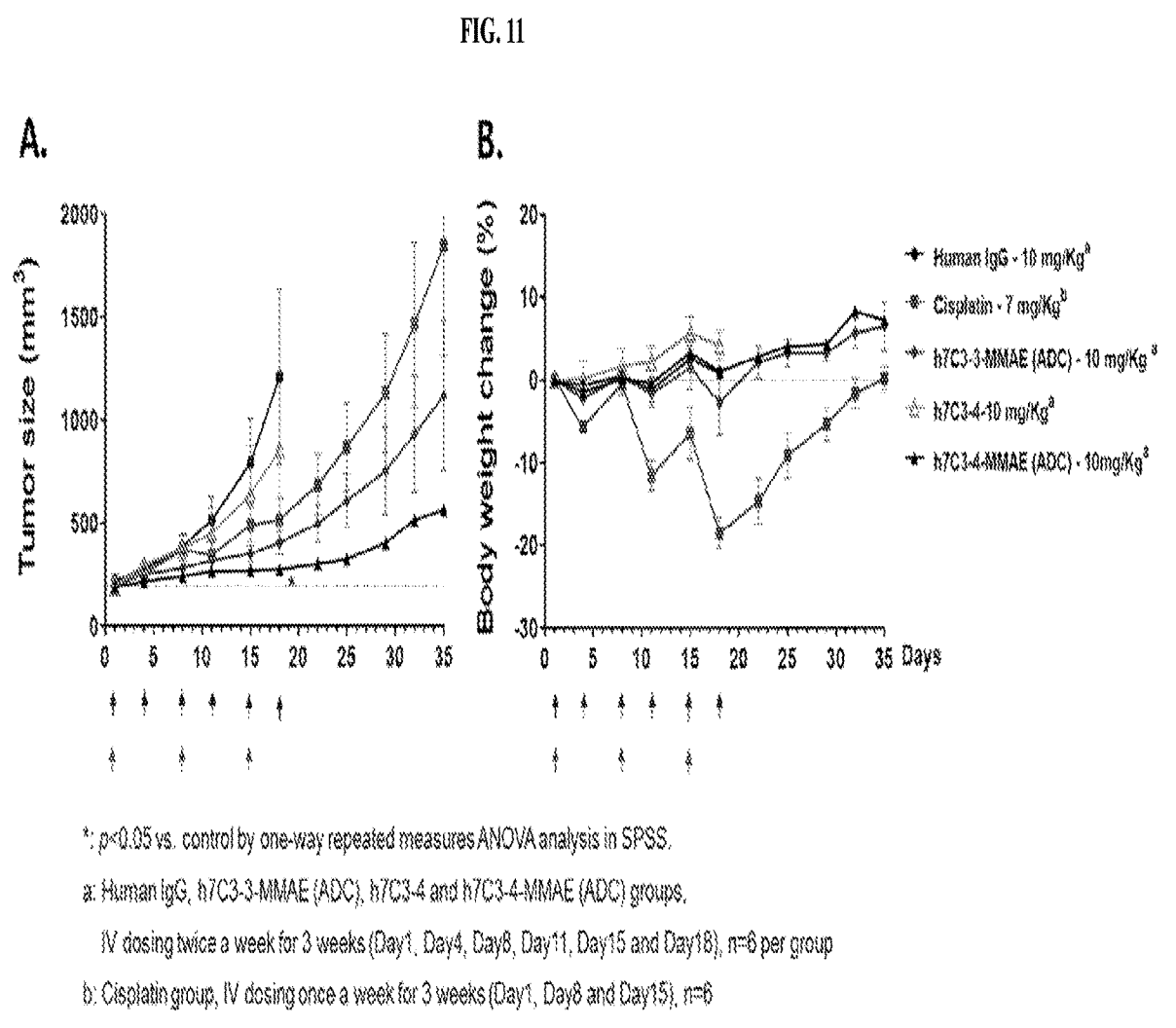

Tumor size ($mm^3$)

2000
1500
1000
500
0

0 5 10 15 20 25 30 35

B.

Body weight change (%)

20
10
0
-10
-20
-30

0 5 10 15 20 25 30 35 Days

Human IgG - 10 mg/Kg[a]

Cisplatin - 7 mg/Kg[b]

h7C3-3-MMAE (ADC) - 10 mg/Kg[a]

h7C3-4-10 mg/Kg[a]

h7C3-4-MMAE (ADC) - 10mg/Kg[a]

*: $p<0.05$ vs. control by one-way repeated measures ANOVA analysis in SPSS.

a: Human IgG, h7C3-3-MMAE (ADC), h7C3-4 and h7C3-4-MMAE (ADC) groups,

IV dosing twice a week for 3 weeks (Day1, Day4, Day8, Day11, Day15 and Day18), n=6 per group b: Cisplatin group, IV dosing once a week for 3 weeks (Day1, Day8 and Day15), n=6

*: $p<0.05$ vs. control by one-way repeated measures ANOVA analysis in SPSS.

a: Human IgG, h7C3-3-MMAE (ADC) and h7C3-4-MMAE (ADC) groups, IV dosing twice a week for 2 weeks (Day1, Day4, Day8 and Day11) , n=8 per group

*: $p<0.05$ vs. control by one-way repeated measures ANOVA analysis in SPSS.

a: No treatment group, n=5 b: h7C3-4-MMAE (ADC) group, IV dosing twice a week for 3 weeks (Day1, Day4, Day8, Day11, Day15 and Day18), n=8

ANTI-HUMAN NEUROTENSIN RECEPTOR 1 ANTIBODY AND USE THEREOF

CROSS REFERENCE

This application is the national stage of International Patent Application No. PCT/US2021/036540, filed on Jun. 9, 2021, which claims priority to U.S. Provisional Application No. 63/036,740, filed on Jun. 9, 2020, the entire contents of which are hereby incorporated by reference herein.

BACKGROUND

Monoclonal antibodies (mAbs) have become important tools in the treatment of diseases such as cancer and infectious diseases, and in several fields including molecular biology, pharmaceutical and medical research. See Baert et al., N Engl J Med, 2003. 348(7): p. 601-8; Cavalli-Bjorkman et al., Med Oncol, 2002. 19(4): p. 277-80; and Plosker and Figgitt, Drugs, 2003. 63(8): p. 803-43. During the past decade, monospecific antibodies targeting specific antigens or cell-surface receptors in different tumor types have achieved substantial success and have been at the forefront of cancer treatment.

Antibody-drug conjugates (ADC) are a new class of highly potent biopharmaceutical drugs consisting of an antibody linked by a chemical linker to a cytotoxic compound. These novel, targeted agents display unique targeting capabilities of antibodies allowing sensitive selection between healthy and cancer tissues with cytotoxic drugs. ADCs represent an innovative therapeutic tool consisting of the high specificity, properties and anti-tumor activity of mAbs that are cancer-specific but not sufficiently cytotoxic, combined with the potent cell killing activity of cytotoxic small molecule drugs that are too toxic to be used on their own. At least five ADCs have received market approval and more than 80 ADCs are currently in clinical trials. See Abdollahpour-Alitappeh, et al., Antibody-drug conjugates (ADCs) for cancer therapy: Strategies, challenges, and successes. J Cell Physiol, 2018. It is highly expected that ADCs will dominate the anti-cancer therapy market in the future with the advancement of cutting-edge technology.

The ligand of neurotensin receptor 1 (NTSR1), neurotensin (NTS), is a short peptide that is found in the nervous system and in peripheral tissues. See Carraway and Leeman, J Biol Chem, 1973. 248(19): p. 6854-61. NTS shows a wide range of biological activities and has important roles in Parkinson's disease and the pathogenesis of schizophrenia, the modulation of dopamine neurotransmission, hypothermia, antinociception, and in promoting the growth of cancer cells. See Bissette, G., et al., Nature, 1976. 262(5569): p. 607-9; Carraway and Plona, Peptides, 2006. 27(10): p. 2445-60; Griebel and Holsboer, Nat Rev Drug Discov, 2012. 11(6): p. 462-78; Kitabgi, Curr Opin Drug Discov Devel, 2002. 5(5): p. 764-76; and Schimpff et al., J Neurol Neurosurg Psychiatry, 2001. 70(6): p. 784-6. Three neurotensin receptors (NTSR) have been identified. NTSR1 and NTSR2 belong to the class A GPCR family, whereas NTSR3 (also called SORT1) is a member of the sortilin family with a single transmembrane domain. See Tanaka et al., Neuron, 1990. 4(6): p. 847-54; Chalon et al., FEBS Lett, 1996. 386(2-3): p. 91-4; and Mazella, Cell Signal, 2001. 13(1): p. 1-6. Most of the known effects of NTS are mediated through NTSR1 which signals preferentially via the Gq protein. See Kitabgi, Curr Opin Drug Discov Devel, 2002. 5(5): p. 764-76.

Neurotensin and its cognate receptor are neuropeptide-receptor complexes frequently deregulated during the neoplastic process. It has been reported that neurotensin receptor 1 (NTSR1) could enhance cancer progression in aggressive malignant solid tumors such as mesothelioma, non—small-cell lung, liver, breast, and head and neck squamous carcinomas. See Alifano et al., Biochimie, 2010. 92(2): p. 164-70; Alifano et al., Clin Cancer Res, 2010. 16(17): p. 4401-10; Wu, Z., et al., Cancer Lett, 2017. 388: p. 73-84; Dupouy et al., PLoS One, 2009. 4(1): p. e4223; and Shimizu et al., Int J Cancer, 2008. 123(8): p. 1816-23. NTSR1 is a promising molecular marker for non—small-cell lung and prostate cancer based on patient tissue staining. See He et al., Eur J Nucl Med Mol Imaging. 2019 46(10): 2199-2207; and Alifano et al., Clin Cancer Res, 2010. 16(17): p. 4401-10. NTSR1 activation also trans-activates the EGFR receptor in colonic, prostatic and pancreatic cancer cell line. See Amorino et al., Oncogene, 2007. 26(5): p. 745-56; and Muller et al., BMC Cancer, 2011. 11: p. 421. Recently, a genome-wide association study also revealed that NTSR1 may have a role in the prognosis of patients with non-small cell lung cancer (NSCLC). See Chang et al., Am J Respir Crit Care Med, 2017. 195(5): p. 663-673. NTS and NTSR1 are abnormally expressed in more than 50% of hepatocellular carcinoma (HCC). Elevated expression of NTS or NTSR1 mRNA is correlated with poor patient outcome. Wu et al., Cancer Lett, 2017. 388: p. 73-84.

Thus, NTSR1 is a potential target for cancer therapy. The carcinogenesis and cancer recurrence may be reduced via inhibiting the activity of NTSR1.

SUMMARY

In one aspect, described herein is an isolated antibody comprising: a heavy chain variable domain ($V_H$) that is at least 75% identical to the amino acid sequence of SEQ ID NO: 1; and a light chain variable domain ($V_L$) that is at least 75% identical to the amino acid sequence of SEQ ID NO: 2; wherein the antibody binds specifically to human neurotensin receptor 1 (hNTSR1). For example, the antibody can bind to the 2nd extracellular loop of hNTSR1.

In some embodiments, the antibody has one or more substitutions within SEQ ID NO: 1 at positions selected from T28, F29, T30, S31, 532A, 151, P53A, N54, S55, G56, N57, T58, Y60, N61, E62, K63, F64, K65, V66A, Y100, D104, and Y105.

In some embodiment, the antibody has one or more substitutions within SEQ ID NO: 2 at positions selected from G96, S97, H98, and P100.

In some embodiments, the antibody includes: heavy chain CDR1: GYTFTSSWIH (SEQ ID NO: 3) or GYAFTSSWIH (SEQ ID NO: 4); heavy chain CDR2: QIRPNSGNTYYNEKFKV (SEQ ID NO: 5); heavy chain CDR3: ARYYYGFDY (SEQ ID NO: 6), ARYHYGFDY (SEQ ID NO: 7), or ARYRYGFDY (SEQ ID NO: 8); light chain CDR1: RSSQSIVHSNGNTYLE (SEQ ID NO: 9); light chain CDR2: KVSNRFS (SEQ ID NO: 10); and light chain CDR3: FQGSHLPWT (SEQ ID NO: 11) or FQGAHLPWT (SEQ ID NO: 12).

In some embodiments, the antibody includes: heavy chain CDR1: GYTFTSSWIH (SEQ ID NO: 3); heavy chain CDR2: QIRPNSGNTYYNEKFKV (SEQ ID NO: 5); heavy chain CDR3: ARYHYGFDY (SEQ ID NO: 7) or ARYRYGFDY (SEQ ID NO: 8); light chain CDR1: RSSQSIVHSNGNTYLE (SEQ ID NO: 9); light chain CDR2: KVSNRFS (SEQ ID NO: 10); and light chain CDR3: FQGSHLPWT (SEQ ID NO: 11).

In some embodiments, the antibody includes: heavy chain CDR1: GYTFTSSWIH (SEQ ID NO: 3); heavy chain CDR2: QIRPNSGNTYYNEKFKV (SEQ ID NO: 5); heavy chain CDR3: ARYHYGFDY (SEQ ID NO: 7) or ARYRYGFDY (SEQ ID NO: 8); light chain CDR1: RSSQ-SIVHSNGNTYLE (SEQ ID NO: 9); light chain CDR2: KVSNRFS (SEQ ID NO: 10); and light chain CDR3: FQGAHLPWT (SEQ ID NO: 12).

In some embodiments, the antibody includes: heavy chain CDR1: GYAFTSSWIH (SEQ ID NO: 4); heavy chain CDR2: QIRPNSGNTYYNEKFKV (SEQ ID NO: 5); heavy chain CDR3: ARYHYGFDY (SEQ ID NO: 7) or ARYRYGFDY (SEQ ID NO: 8); light chain CDR1: RSSQ-SIVHSNGNTYLE (SEQ ID NO: 9); light chain CDR2: KVSNRFS (SEQ ID NO: 10); and light chain CDR3: FQGAHLPWT (SEQ ID NO: 12).

In some embodiments, the antibody includes heavy chain CDR1: GYTFTSSWIH (SEQ ID NO: 3); heavy chain CDR2: QIRPNSGNTYYNEKFKV (SEQ ID NO: 5); heavy chain CDR3: ARYYYGFDY (SEQ ID NO: 6); light chain CDR1: RSSQSIVHSNGNTYLE (SEQ ID NO: 9); light chain CDR2: KVSNRFS (SEQ ID NO: 10); and light chain CDR3: FQGSHLPWT (SEQ ID NO: 11).

In some embodiment, the isolated antibody includes: heavy chain CDR1: GYAFTSSWIH (SEQ ID NO: 4); heavy chain CDR2: QIRPNSGNTYYNEKFKV (SEQ ID NO: 5); heavy chain CDR3: ARYHYGFDY (SEQ ID NO: 7); light chain CDR1: RSSQSIVHSNGNTYLE (SEQ ID NO: 9); light chain CDR2: KVSNRFS (SEQ ID NO: 10); and light chain CDR3: FQGAHLPWT (SEQ ID NO: 12).

In some embodiments, the antibody includes a $V_H$ sequence that is the sequence of SEQ ID NO: 13; and a $V_L$ sequence that is the sequence of SEQ ID NO: 14.

In some embodiments, the antibody includes a $V_H$ sequence that is the sequence of SEQ ID NO: 15; and a $V_L$ sequence that is the sequence of SEQ ID NO: 16.

In some embodiments, the antibody is a recombinant antibody, a monoclonal antibody, a chimeric antibody, a humanized antibody, an IgG1 antibody, or an antibody fragment comprising an antigen-binding site.

In another aspect, provided herein is an antibody conjugate comprising any of the anti-hNTSR1 antibodies described herein and a non-antibody molecule.

In some embodiments, the non-antibody molecule is a polypeptide, polymer, oligosaccharide, lipid, glycolipid, solid support, small molecule drug, biotin, nucleic acid molecule, carrier protein, or detectable label.

In some embodiments, the antibody conjugate is an antibody-drug conjugate and the non-antibody molecule is a cancer drug for inhibiting a cancer cell or treating a tumor that expresses hNTSR1. For example, the cancer drug can be monomethyl auristin E (MMAE).

In some embodiments, the tumor is a mesothelioma, lung tumor, breast tumor, head and neck squamous carcinoma, colon tumor, pancreatic tumor, prostate tumor, or liver carcinoma.

In yet another aspect, described herein is a pharmaceutical composition comprising any of the antibody or antibody-drug conjugates described herein and a pharmaceutical carrier.

In one aspect, described herein is a method of treating a tumor in a subject comprising administering any of the antibody-drug conjugates or pharmaceutical compositions described herein to a subject in need thereof. In some embodiments, the tumor expresses hNTSR1.

In some embodiments, the tumor is a mesothelioma, lung tumor, breast tumor, head and neck squamous carcinoma, colon tumor, pancreatic tumor, prostate tumor, or liver carcinoma.

In another aspect, a method of detecting NTSR1 in a sample or a tissue or cell expressing NTSR1 is described herein. The method includes: contacting a sample, tissue or cell with any of the antibodies or antibody conjugates described herein, and determining binding of the antibody or antibody conjugate to a target in the sample, or to the tissue or cell.

In yet another aspect, described herein is an isolated nucleic acid molecule encoding any of the antibodies described herein or a component thereof.

The details of one or more embodiments are set forth in the accompanying drawing and the description below. Other features, objects, and advantages of the embodiments will be apparent from the description and drawing, and from the claims.

BRIEF DESCRIPTION OF DRAWINGS

FIG. 1 is a set of graphs showing characterization of 7C3 mAb. (A) The binding of 7C3 mAb to cyclic ECL2 peptide of NTSR1 in ELISA. (B) Binding of 7C3 (10 μg/ml) to NTSR1 on A549 cells measured with flow cytometry.

FIG. 2 is a graph showing affinity and kinetics data of h7C3-3. The binding affinity between h7C3-3 and NTSR1 ECL2 peptide was determined by surface plasmon resonance (SPR).

FIG. 5 shows characterization of humanized h7C3-4 and h7C3-5 antibodies. Heavy chain (A) and light chain (B) amino acid sequence alignments of h7C3-4 and h7C3-5. The mutated residues are indicated in bold and the CDR sequences are defined according to the Kabat definition. (C) Binding of h7C3-4 and h7C3-5 to NTSR1 on A549 cells measured with flow cytometry. h7C3-4 heavy chain (SEQ ID NO: 13); h7C3-4 light chain (SEQ ID NO: 14); h7C3-5 heavy chain (SEQ ID NO: 15); h7C3-5 light chain (SEQ ID NO: 16).

FIG. 8 is a set of graphs showing the in vitro cytotoxic effect of h7C3-3-MMAE in various cancer cell lines.

FIG. 11 is a set of graphs showing efficacies of h7C3-3-MMAE, h7C3-4, and h7C3-4-MMAE at a dose of 10 mg/kg compared with Cisplatin at a dose of 7 mg/kg in the H1299 lung tumor xenograft model. (A) Antitumor efficacies of h7C3-3-MMAE and h7C3-4-MMAE are shown with changes in tumor volumes. (B) Both groups did not show body weight loss.

DETAILED DESCRIPTION

Figure 3:
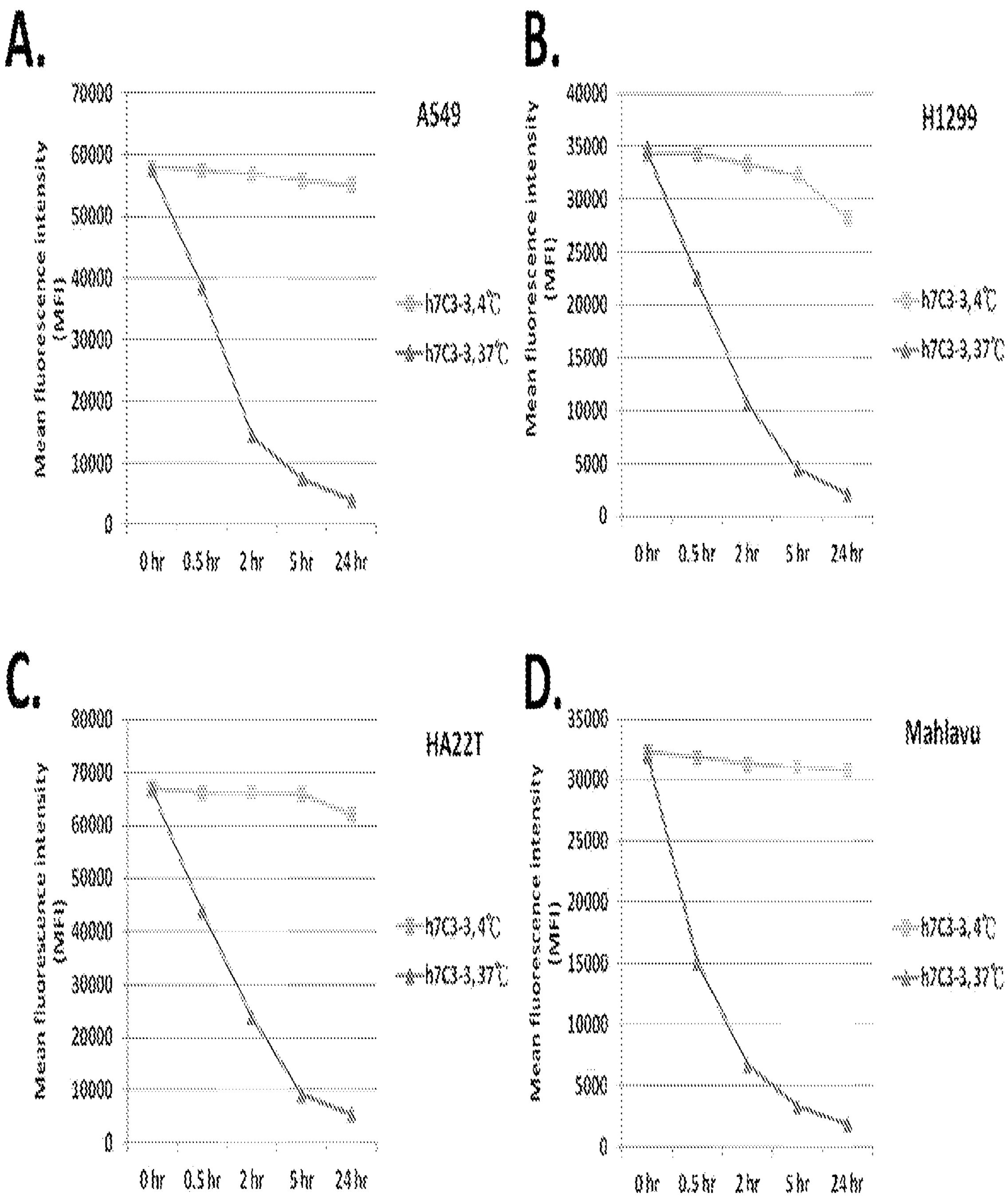
FIG. 3 is a set of graphs showing internalization of anti-NTSR1 mAbs on various cancer cell lines overexpressing NTSR1. Flow cytometry analysis of (A) A549, (B) H1299, (C) HA22T, and (D) Mahlavu cells treated with different antibodies (10 μg/ml) at 4° C. or 37° C., respectively.

Described herein are novel antibodies that bind to human NTSR1 and conjugates thereof.

Each of the anti-NTSR1 antibodies can include a heavy chain variable domain ($V_H$) that is at least 75% (e.g., at least 78%, at least 79%, at least 80%, at least 85%, at least 90%, at least 95%, or at least 98%) identical to the amino acid sequence of SEQ ID NO: 1, and a light chain variable domain ($V_L$) that is at least 75% (e.g., at least 78%, at least 79%, at least 80%, at least 85%, at least 90%, at least 95%, or at least 98%) identical to the amino acid sequence of SEQ ID NO: 2.

```
                                      SEQ ID NO: 1
QVQLQQPGSVLVRPGASVKLSCKASGYTFTSSWIHWAK

QRPGQGLEWIGQIRPNSGNTYYNEKFKVKATLTVDTSS

STAYVDLSSLTSEDSAVYYCARYYYGFDYWGQGTLVTV

SS
```

-continued

```
                                      SEQ ID NO: 2
DVLMTQTPLSLPVSLGDQASISCRSSQSIVHSNGNTYL

EWYLQKPGQSPKLLIYKVSNRFSGVPDRFSGSGSGTDF

TLKISRVEAEDLGVYYCFQGSHLPWTFGGGTKLEIKR
```

The antibodies each can have one or more substitutions within SEQ ID NO: 1 at positions selected from T28, F29, T30, S31, S32A, 151, P53A, N54, S55, G56, N57, T58, Y60, N61, E62, K63, F64, K65, V66A, Y100, D104, and Y105. In addition to or alternatively, the antibody can have one or more substitutions within SEQ ID NO: 2 at positions selected from G96, S97, H98, and P100. The amino acid substitution can be any amino acid (e.g., Ala) as long as the substitution does not significantly decrease the binding affinity of the antibodies for NTSR1 (e.g., by no more than 25%, 20%, 15%, 10%, or 5%) as compared to an antibody having the sequences of SEQ ID NOs: 1 and 2. The binding affinity of an antibody to NTSR1 can be determined using various methods known in the art or described herein, e.g., binding to NTSR1 on a cell or to ECL2 peptide.

In some embodiments, the anti-NTSR1 antibody has a heavy chain CDR1 having the sequence of GYTFTSSWIH (SEQ ID NO: 3) or GYAFTSSWIH (SEQ ID NO: 4); a heavy chain CDR2 having the sequence of QIRPNSGNTYYNEKFKV (SEQ ID NO: 5); a heavy chain CDR3 having the sequence of ARYYYGFDY (SEQ ID NO: 6), ARYHYGFDY (SEQ ID NO: 7), or ARYRYGFDY (SEQ ID NO: 8); a light chain CDR1 having the sequence of RSSQSIVHSNGNTYLE (SEQ ID NO: 9); a light chain CDR2 having the sequence of KVSNRFS (SEQ ID NO: 10); and a light chain CDR3 having the sequence of FQGSHLPWT (SEQ ID NO: 11) or FQGAHLPWT (SEQ ID NO: 12).

In some embodiments, the antibody (e.g., h7C3-1) has GYTFTSSWIH (SEQ ID NO: 3); QIRPNSGNTYYNEKFKV (SEQ ID NO: 5); ARYHYGFDY (SEQ ID NO: 7) or ARYRYGFDY (SEQ ID NO: 8); RSSQSIVHSNGNTYLE (SEQ ID NO: 9); KVSNRFS (SEQ ID NO: 10); and light chain CDR3: FQGSHLPWT (SEQ ID NO: 11).

In some embodiments, the antibody (e.g., h7C3-2) has GYTFTSSWIH (SEQ ID NO: 3); QIRPNSGNTYYNEKFKV (SEQ ID NO: 5); ARYHYGFDY (SEQ ID NO: 7) or ARYRYGFDY (SEQ ID NO: 8); RSSQSIVHSNGNTYLE (SEQ ID NO: 9); KVSNRFS (SEQ ID NO: 10); and FQGAHLPWT (SEQ ID NO: 12).

In some embodiments, the antibody (e.g., h7C3-3, h7C3-4, or h7C3-5) includes

```
                          (SEQ ID NO: 4)
GYAFTSSWIH;

                          (SEQ ID NO: 5)
QIRPNSGNTYYNEKFKV;

                          (SEQ ID NO: 7)
ARYHYGFDY
or

                          (SEQ ID NO: 8)
ARYRYGFDY;
```

-continued (SEQ ID NO: 9)
RSSQSIVHSNGNTYLE;

(SEQ ID NO: 10)
KVSNRFS;
and (SEQ ID NO: 12)
FQGAHLPWT.

In some embodiments, the antibody (e.g., h7C3) has GYTFTSSWIH (SEQ ID NO: 3); QIRPNSGNTYYNEKFKV (SEQ ID NO: 5); ARYYYGFDY (SEQ ID NO: 6); RSSQSIVHSNGNTYLE (SEQ ID NO: 9); KVSNRFS (SEQ ID NO: 10); and FQGSHLPWT (SEQ ID NO: 11).

In some embodiments, the antibody includes a $V_H$ having the sequence of SEQ ID NO: 13 or 15, and a $V_L$ having the sequence of SEQ ID NO: 14 or 16.

SEQ ID NO: 13
QVQLQQPGTVLVRPGASVKLSCKASGYAFTSSWIHWA

KQRPGQGLEWIGQIRPNSGNTYYNEKFKVKATLTVDT

SSSTAYVELSSLTSEDSAVYYCARYHYGFDYWGQGTL

VTVSS

SEQ ID NO: 14
DVLMTQTPLSLPVSLGDQASISCRSSQSIVHSNGNTY

LEWYLQKPGQSPKLLIYKVSNRFSGVPDRFSGSGSGT

DFTLTISRVEAEDLGVYYCFQGAHLPWTFGGGTKLEI

KR

SEQ ID NO: 15
QVQLVQSGAEVKKPGASVKVSCKASGYAFTSSWIHWV

RQAPGQRLEWMGQIRPNSGNTYYNEKFKVRVTITRDT

SASTAYMELSSLRSEDTAVYYCARYHYGFDYWGQGTL

VTVSS

SEQ ID NO: 16
DIVMTQTPLSLSVTPGQPASISCRSSQSIVHSNGNTY

LEWYLQKPGQSPQLLIYKVSNRFSGVPDRFSGSGSGT

DFTLKISRVEAEDVGVYYCFQGAHLPWTFGGGTKVEI

KR

The term "antibody" as used herein includes various antibody structures that have an antigen-binding activity, including but not limited to monoclonal antibodies, polyclonal antibodies, full-length antibodies or fragments thereof, antibodies that contain an Fc region, Fab fragments, Fab' fragments, F(ab')2 fragments, single-chain antibodies, scFV multimers, monovalent antibodies, multivalent antibodies, humanized antibodies, and chimeric antibodies.

Based on the antibody CDR sequences disclosed herein, a skilled practitioner would be able to produce an anti-NTSR1 antibody in various forms using methods known in the art, e.g., recombinant methods.

Also contemplated herein is an isolated nucleic acid molecule (e.g., an expression vector) encoding one of the anti-NTSR1 antibodies described herein or a component thereof. A host cell containing the nucleic acid is also provided herein. The nucleic acid molecule and host cell can be used to generate the anti-NTSR1 antibody.

Any of the anti-NTSR1 antibodies described herein can be conjugated to a non-antibody molecule to form an antibody conjugate using methods known in the art. The non-antibody molecule can be, for example, a polypeptide, polymer, oligosaccharide, lipid, glycolipid, solid support (e.g., a bead or plate), small molecule drug (e.g., a cytotoxic drug), biotin, nucleic acid molecule, carrier protein, or detectable label (e.g., a fluorescent label). The non-antibody molecule can be linked to the antibody via a cleavable linker (e.g., valine-citrulline) or a non-cleavable linker (e.g., N-Maleimidomethylcyclohexane-1-carboxylate (MCC) or Maleimidocaproyl Mercaptoacetamidocaproyl). Such antibody conjugates can be used for various purposes such as treating cancers or detecting NTSR1 in samples.

In some embodiments, the antibody conjugate is an antibody-drug conjugate, in which the drug is for inhibiting a cancer cell or treating a tumor, e.g., a cancer cell or tumor that expresses NTSR1. In some embodiments, the drug is monomethyl auristin E (MMAE).

Any of the antibodies or antibody conjugates described herein can be used to inhibit binding between NTSR1 and its ligands, inhibit an NTSR1 function, detect an NTSR1 protein or a fragment thereof in a sample (e.g., in an immunoassay), bind to a tissue or cell that expresses NTSR1 (e.g., to identify a cell or to isolate an NTSR1-expressing cell), inhibit the growth of a cancer cell or tumor, or treat a cancer in a subject.

The term "sample" can be any biological sample, e.g., a bodily fluid sample, a blood sample, a cell sample, a urine sample, a saliva sample, or a tissue sample.

Tumors that express NTSR1 can be potential targets of the anti-NTSR1 antibodies or conjugates thereof. Such tumors include, but are not limited to, mesothelioma, lung tumor, breast tumor, head and neck squamous carcinoma, colon tumor, pancreatic tumor, prostate tumor, or liver carcinoma. Optionally, before administering any of the anti-NTSR1 antibodies or conjugates to a subject, it can be determined whether the tumor in the subject expresses NTSR1. The treatment method can be performed alone or in conjunction with other drugs or therapy.

A "subject" refers to a human or a non-human animal. "Treating" or "treatment" refers to administration of a compound or composition to a subject, who has a disorder, with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound or composition that is capable of producing a medically desirable result in a treated subject.

Any of the anti-NTSR1 antibodies and antibody conjugates described herein can be formulated as a pharmaceutical composition suitable for various routes of administration, e.g., intravenous, intraarticular, conjunctival, intracranial, intraperitoneal, intrapleural, intramuscular, intrathecal, or subcutaneous route of administration. The pharmaceutical composition can be an aqueous solution or lyophilized formulation. It can contain a pharmaceutically acceptable carrier, e.g., a buffer, excipient, stabilizer, or preservative. The pharmaceutical composition can include other active ingredients that work together with the antibody or antibody-conjugate, e.g., another therapeutic agent or an adjuvant.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

Example 1: Materials and Methods

Cell Lines

A549 (NSCLC) cells were maintained in F-12K medium (Gibco, Grand Island, NY, USA) with 10% fetal bovine serum (Gibco, Grand Island, NY, USA). H1299 (NSCLC) cells were maintained in RPMI medium supplemented with 10% FBS and 2 mM L-glutamine HA22T (HCC) were maintained in DMEM medium supplemented with 10% FBS, 0.1 mM non-essential amino acids and 2 mM L-glutamine (Gibco). Mahlavu were maintained in DMEM medium supplemented with 10% FBS. PC-3 (PCa) cells were maintained in RPMI1640 medium (Gibco, SH30027) supplemented with 10 mM HEPES, 1 mM sodium pyruvate (Gibco), 4.5 g/L glucose and 10% FBS.

Immunization of Mice and RNA Purification

Five female BALB/c mice (4-6 weeks old) were given intraperitoneal injections of 0.1 mg of ovalbumin conjugated ECL2 peptide every two weeks for 12 weeks. Blood samples were collected 1 week after each immunization and titrated by indirect Enzyme-Linked Immunosorbent Assay (ELISA). After a total of six boosts, the mice were sacrificed to exercise the spleen. Cells were solubilized, and total mRNA was produced from the mice with RNeasy protect midi kit (Qiagen, Germany) according to the manufacturer's instructions. RT-PCR amplification of heavy chain and kappa chain purification Total RNA of the harvested mice spleen was extracted with Trizol Reagent according to the manufacturer's procedure (Invitrogen, USA). Purity and concentration were determined by measuring the absorbance (A) at 260 nm and 280 nm (A260/A280). First strand cDNA was generated from 350 ng of mRNA (Oligotex mRNA Mini kit, QIAGEN) using reverse transcriptase (Roche) with a mix of 1 μl of RNaseOut (40 U/μl, Invitrogen) and MuJH (or MuJK)-FOR primer.

Construction of the Phage Display scFv Library

Briefly, the library construction process consisted of three steps: (i) amplification of the VH and VL domains using framework region family-specific primers, (ii) re-amplification of each segment with primers containing the linker segment, (iii) assembly of both segments (VH and VL) by overlap extension polymerase chain reaction (PCR). All PCR reactions were performed with TaKaRa Ex Taq polymerase (RR001A) and primers specific to murine heavy chain and Kappa light chain. See Benhar and Reiter, Curr Protoc Immunol, 2002. Chapter 10: p. Unit 10 19B.

PCR products containing scFvs were digested with excessive restriction enzymes EcoRI and NcoI (NEB), and about 10.0 μg was ligated overnight with 40.0 μg of EcoRI/NcoI-linearlized pHEN2 vector (purified by agarose gel extraction) in a total volume of 100 μl with 2400 units of T4 DNA ligase (NEB) at 16° C. Following ligation, the recombinant DNA was precipitated, washed and dissolved in 20 μl of distilled water. 1 μl of recombinant DNA was transformed by electroporation into 25 μl of *E. coli* TG1 (Lucigen) every time. After transformation, 20 ml Recover medium (Lucigen) was added and the culture was shaken for 1 h at 37° C., and then 200 ml of 2YT containing 100 μg/ml ampicillin was cultivated for an additional 16~18 hour at 37° C. on a shaker. At this point, culture aliquots were plated on 2YT agar/ampicillin to titer library size, which was calculated by counting the number of ampicillin resistant colonies. Phagemids containing the scFv were prepared from this overnight culture. Approximately M13K07 ($10^{12}$ pfu) helper phage was added to TG1 samples containing scFv gene libraries and incubated for 2~3 h at 37° C. with shaking. 50 μg/m1Kanamycin was added to and the culture was shaken overnight at 30° C. The cells were centrifuged at 4000 rpm for 20 min at 4° C. The supernatant was mixed with 50 ml 20% PEG 8000/2.5 M NaCl and incubated on ice for 60 minutes, and then phages were precipitated by centrifugation at 8000 rpm for 20 minutes at 4° C. The supernatant was discarded and the pellet drained. The phages were resuspended in 1 ml PBS, vortexed and centrifuged at 13000 rpm for 10 minutes to pellet debris. The supernatant was stored at 4° C. or used directly for the next round of biopanning.

Affinity Selection (Panning) of Phages

Streptavidin-coated magnetic beads were prewashed with 10 volumes of TBS containing 2% (wt/vol) BSA and 0.02% (wt/vol) NaN3, and the washed beads were suspended in TBS containing 2% (wt/vol) BSA, 5 mM DTT and 0.02% (wt/vol) NaN3. Non-specific binding of the scFv phage library was depleted with streptavidin beads in a final volume of 500 ul in a 1.5-ml microcentrifuge tube (mix $2\times10^{12}$ phage particles in 500 ul of 4% (wt/vol) BSA in TBS plus 1% (vol/vol) Tween-20 and 10 mM DTT), and then 60 μl of prewashed streptavidin beads was added and incubated overnight at 4° C. Next, 0.4 μg of the Biotin-human NTSR1 linear ECL2 peptide in 3 ml of lx TBS, 2% (wt/vol) BSA, 0.5% (vol/vol) Tween-20 and 5 mM DTT was added to 2 ml of pre-adsorbed phage particles ($2\times10^{12}$ phage particles), and the mixture was incubated in the immune-tube for 4 hours at room temperature (RT). After the twice panning cycle, individual colonies of phagemid-carrying cells were used to prepare monoclonal phages in sterile 96-well plates (Nunc, Sweden) that were screened by ELISA.

Phage ELISA

Ninety-six-well NeutrAvidin Coated Plates (Pierce) were loaded with 100 ml of 5 mg/ml of the Biotin-human NTSR1 linear ECL2 peptide in wash buffer (25 mM Tris, 150 mM NaCl, 0.1% BSA, 0.05% Tween20 PH7.2). On the following day, the plates were washed with wash buffer and blocked with 5% skimmed milk in wash buffer for 1 hour at RT. After additional washing with wash buffer, 100 μl of freshly prepared phages were added per well and incubated for 1 hour at RT. The plates were washed again with wash buffer, and 1:5000 diluted anti-M13 antibody (ab24229) was placed in each well for 1 hour at RT, followed by additional washes with wash buffer. 1:5000 diluted Goat Anti-Mouse IgG-HRP (Jackson, 115-035-003) was placed in each well for 1 hour at RT, followed by additional washes with wash buffer. Finally, addition of 100 μl of 3, 3', 4, 4'—tetramethylbenzidine (TMB) (HRP substrate) solution (Pierce) was added to each well and incubated at RT. The reaction was stopped by the addition of 100 μl of 1M H2SO4 to each well. The plate was analyzed with a plate reader (Discover X reader) at 450 nm.

Construction and Expression of Antibody

The sequences of the variable domains of the heavy chain ($V_H$) and light chain ($V_L$) of 7C3 were fused to the sequences of the constant domains of the human IgG1 heavy chain and human IgG(κ) light chain encoded in the pFUSE-CHIg-hG1 and pFUSE2-CLIg-hK vectors from InvivoGen, respectively. Expression of the human-mouse chimeric antibody was achieved by transfecting the vectors into Expi293 cell. The secreted antibody were then purified from the culture supernatant by Protein A affinity chromatography and tested to determine if it still retained the antigen-binding capacity after chimerization.

Affinity Maturation Via Site-Directed Mutagenesis

All mutations were introduced into variable domain of heavy chain ($V_H$) or light chain ($V_L$) using overlap extension PCR mutagenesis. Mutated coding regions for $V_H$ and $V_L$ were amplified by PCR using specific primers. PCR products were annealed via their common overlap and amplified in a second PCR reaction, then purified and ligated into the pFUSE-CHIg-hG1 or pFUSE2-CLIg-hK vectors, respectively. After transformation of *E. coli* JM109 (ECOS™ 9-5), individual colonies were screened by digestion with the appropriate restriction enzymes for each individual mutant. Putative mutants identified by this analytical restriction enzyme digest were confirmed by sequencing.

NTSR1-Binding Affinity Assay

The NTSR1-binding capacity of different antibodies were measured by ELISA. Briefly, NeutrAvidin 96-well plates (Pierce Cat:15128) were coated with cyL2-Biotin peptides at a final concentration of 5 μg/ml at RT for 1 hour. On the following day, the coating solution was removed, and the plates were blocked with 5% (v/v) non-fat dry milk in phosphate buffer saline (PBS) for 1 hour. After washing with PBST, gradient concentrations of anti-NTSR1 antibodies were added in triplicate. After 1 hour of incubation, the plate was washed three times with PBST, followed by the addition of horseradish peroxidase (HRP)-conjugated goat anti-human IgG Fc antibody (100 μL) into each well for an additional hour at RT. Finally, 100 μL of tetramethylbenzidine (TMB) substrate was added into each well to produce color for visualization. After 2 minutes of incubation, 100 μL of 2M H2SO4 was used to stop the reaction. The absorbance of each well was read at 450 nm with a plate reader. Flow cytometry A total of $1\times10^6$ cells were reacted with an anti-NTSR1 antibody in 100 μL of FACS buffer (PBS containing 0.5% BSA) for 60 minutes at 4° C. and washed two times to remove excess antibody. Secondary FITC (BD Pharmingen™) conjugated mouse anti-human IgG antibodies were incubated for an additional 60 minutes on ice. Cells were washed again and followed by an additional incubation with 1 ml PBS containing 0.5 mg/mL propidium iodide at 4° C. for 10 minutes. Data were collected on 10,000 living cells by FACS (Bio-Red S3e cell sorter). Fluorescence intensity from channel FL-1 was calculated with Flow Jo flow 0 cytometry analysis software.

Surface Plasmon Resonance

The interaction of NTSR1-specific mAbs with extracellular loop 2 (ECL2) peptides of NTSR1 was measured by surface plasmon resonance using an Open SPR (Nicoya, Canada) instrument. Biotin-conjugated ECL2 peptides were immobilized on a streptavidin-coated sensor chip by injecting the peptides diluted in HBS-EP5 buffer saline (20 mM HEPES, 250 mM NaCl, 3 mM EDTA, 0.05% Tween 20 and 0.5% BSA, pH 7.4) at a concentration of 10 μg/ml at a flow rate of 30 μl/min. For kinetic experiments, NTSR1-specific mAbs diluted in HBS-EP5 at concentrations ranging from 24 to 1.5 nM were injected at a flow rate of 30 μl/min over the immobilized ECL2 peptides. Binding of the NTSR1-specific mAbs at different concentrations to the immobilized ECL2 peptides were analyzed using the TraceDrawer software (Nicoya, Canada). Association rate (ka), dissociation rate (kd), and affinity (KD) were calculated using global analysis, fitting the data to a simple 1:1 binding model.

Internalization of NTSR-1 Antibody in Different NTSR1-Expressing Cell Lines (Flow Cytometry)

NTSR-1 antibody was used for flow cytometry analysis to compare the NTSR1 expression level in different lung and HCC cell lines, including A549, H1299, HA22T and Mahlavu. A total of $1\times10^6$ cells were reacted with the h7C3-3 antibody in FACS buffer for 60 minutes at 4° C. and washed two times to remove excess antibody. Cells were then transferred to 4° C. or 37° C. for 0, 0.5, 2, 5, 24 hours and followed by an additional incubation with secondary anti-human IgG Fc-PE (BioLegend) antibody for 60 minutes at 4° C. Cells were washed again, and data were collected by BD LSRFortessa. Fluorescence intensity from channel FL-1 was calculated with Flow Jo flow cytometry analysis software.

Internalized of h7C3-3 or h7C3-3-ADC Antibodies in A549 Cells (Flow Cytometry)

A total of $1\times10^6$ cells were reacted with the indicated antibody or ADC in 100 μL of FACS buffer for 60 minutes at 4° C. and washed to remove excess antibody or ADC. Cells were then transferred to 4° C. or 37° C. for 90 minutes. To determine the relative number of h7C3-3 or h7C3-3-ADC on the cell surface, cells were stained with saturating amounts of FITC (BD Pharmingen™) conjugated mouse anti-human IgG antibodies and incubated for additional 60 minutes on ice. Cells were washed again and followed by an additional incubation with 1 ml PBS containing 0.5 mg/mL propidium iodide at 4° C. for 10 minutes. Data were collected on 10,000 living cells by FACS (Bio-Red S3e cell sorter). Fluorescence intensity from channel FL-1 was calculated with Flow Jo flow cytometry analysis software. Preparation of anti-NTSR1 antibody-drug conjugates (ADCs)

h7C3-3 or h7C3-4 was treated with 0.1 molar equivalent of TCEP-HCl (Tris(2-Carboxyethyl) phosphine hydrochloride, Sigma-Aldrich) in 50 mM HEPES (4-(2-hydroxyethyl)-1-piperazineethanesulfonic acid buffer, Sigma-Aldrich), pH 6.9 and 1 mM ethylenediaminetetraacetic acid (EDTA, Sigma-Aldrich) for 2 hours at 37° C. The reduced antibodies were reacted with vcMMAE(Achemblock, Q70231) for 60 minutes at RT. The unreacted vcMMAE was quenched using 1 mM N-acetyl-L-cysteine (Sigma-Aldrich) and incubated for 30 minutes at RT. The reaction mixture was then buffer-exchanged into PBS (pH 6.9) using Amicon Ultrafree centrifugal filter units (Millipore).

Hydrophobic Interaction Chromatography (HIC) Analysis

The characterization of h7C3-3 and h7C3-3 ADCs was carried out using HIC as follows: 1200 HPLC (Agilent Technologies); TSKgel Butyl-NPR column (4.6×35 mm, particle size 2.5 μm; TOSOH,); solvent A, 1.5 mol $L^{-1}$ ammonium sulfate and 25 mM phosphate (pH=6.95); solvent B, 75% (V/V) 25 mM phosphate, 25% (V/V) isopropanol (pH=6.95); the gradient was 100% A to 100% B over 15 minutes; 0.5 mL $min^{-1}$ flow rate; column temperature at 25° C.; UV detection wavelength of 280 nm.

In Vitro Cell Cytotoxicity Assay

The number of living cells were determined using the CellTiter-Glo® Luminescent Cell Viability Assay (Promega G7571). Cells were plated in 96-well opaque Costar plates (Cat number 136101). In brief, 500-2500 cells in 90 μL media were added to each well in quadruplicate and allowed to adhere for 16 hours. Anti-NTSR1 (dose range: 0-500 nM), anti-NTSR1-MMAE (dose range: 0-500 nM) or Paclitaxel (dose range: 0-100 nM) were added in 10 After 72-120 hours, medium was removed, and 200 μL of CellTiter-Glo® viability reagent contain culture medium (1:1) was added to each well and placed on an orbital shaker in the dark for 2 minutes. The plate was allowed to sit at RT for 10 minutes before being read on a GloMax® Explorer Multimode Microplate Reader (GM3500).

Pharmacokinetics

The pharmacokinetics of h7C3-3 and h7C3-4 were evaluated in B6 mice. B6 mice (n=6) were administered 10 mg/kg of test material (based on the antibody component) by tail vein injection. Blood samples were collected from each mouse via the saphenous vein at hour 1, 2, and 6, and at day 1, 2, 3, 4, 7, 9, 11, 14, 16, 18, 21, 23, 25, 35 and 42 post-injection, and serum samples were collected. Plasma concentrations of h7C3-3 and h7C3-4 were measured by IgG (Total) Human ELISA Kit (Invitrogen, BMS2091).

Mouse Xenograft Tumor Model and Antibody-Drug Conjugates (ADC) Treatment

Immuodeficient male NU/NU nude mice (for H1299 and PC-3 xenograft study) and male Fox Chase SCID® mice (for HA22T-Luc xenograft study) of 7-week-old purchased from BioLASCO were housed in sterilized cages equipped with an air filter and sterile bedding materials at the Laboratory Animal Center of the National Health Research Institutes (NHRI), which is an AAALAC International accredited facility. All mice were fed with sterilized water and chow ad libitum under 12-hour light/12-hour dark cycle throughout the study. On the day of tumor cell inoculation, the number of viable cells was counted by using a hemocytometer with trypan blue staining under a light microscope. Cells were suspended in phenol red-free medium [RPMI1640 (H1299) or DMEM (HA22T-Luc)] or PBS (PC-3) and Matrigel™ (356237, Matrigel® Matrix, Corning, MA, United States) in 1:1 ratio. H1299 ($1\times10^6$ cells), HA22T-Luc ($5\times10^6$ cells) and PC-3 ($1\times10^6$ cells) were implanted subcutaneously into the left flank of either nude or SCID mice using a 1 mL syringe (needle 24G×1 inch). Tumor dimensions were measured with a digital caliper, and the tumor volume in $mm^3$ was calculated by the formula: Volume=(length×width^2)/2. Tumor-bearing mice were grouped (n=5-8 per group) and administered when the average tumor volume was approximately at 200 $mm^3$. In the 3 individual xenograft studies, human IgG (HU-GF-ED, Lot#120916DG, Molecular Innovations, MI, USA), h7C3-4, h7C3-3-MMAE and h7C3-4-MMAE were diluted in 1× Dulbecco's Phosphate Buffered Saline (02-023-5A, Biological Industries, CT, USA) freshly before dosing at concentration of 2.5 mg/ml. Cisplatin (KEMOPLAT, 1 mg/mL, 87200009AA, Fresenius Kabi, Bad Homburg, Germany) was purchased. In the H1299 xenograft study, tumor-bearing mice were divided into 5 groups (6 mice per group): Human IgG −10 mg/Kg group (negative control), Cisplatin—7 mg/Kg group (positive control), h7C3-3-MMAE —10 mg/Kg group, h7C3-4 −10 mg/Kg group and h7C3-4-MMAE −10 mg/Kg group. The mice were intravenously injected with 4 mL/Kg of dose volume by tail vein twice per week for 3 weeks, except for the Cisplatin group, which was once per week for 3 weeks. In the HA22T-Luc xenograft study, tumor-bearing mice were divided into 3 groups (8 mice per group): Human IgG −10 mg/Kg group (negative control), h7C3-3-MMAE −10 mg/Kg group and h7C3-4-MMAE (ADC) −10 mg/Kg group. The mice were intravenously injected with 4 mL/Kg of dose volume by tail vein twice per week for 2 weeks. In the PC-3 xenograft study, tumor-bearing mice were divided into 2 groups: no treatment group (5 mice) and h7C3-4-MMAE (ADC) −10 mg/Kg (8 mice). The mice in h7C3-4-MMAE −10 mg/Kg group were intravenously injected with 4 mL/Kg of dose volume by tail vein twice per week for 3 weeks. Each treatment was based on the body weight. Body weight and tumor size were measured twice weekly.

Immunohistochemistry

Deparaffinized tissue sections (4 μm) were subjected to heat-induced epitope retrieval in Tris-EDTA buffer (pH 9) at 95° C. for 30 minutes. The sections were blocked with inhibitor CM at 37° C. for 4 minutes. The slides were incubated with primary antibody including 2 μg/ml anti-NTSR1-B12 (SC-376958, Santa Cruz Biotechnology) and different anti-anti-NTSR1 antibody clones (7C3, h7C3-2 and h7C3-3) for 1 hour. The slides were then incubated with appropriate secondary antibodies; OmniMap anti-mouse-HRP for anti-NTSR1-B12 and anti-human-HRP for 7C3, h7C3-2 and h7C3-3 at RT for 30 minutes. The staining was performed with diamino-benzidine tetrahydrochloride.

Example 2: Characterization of 7C3 Antibody

Antibodies to human NTSR1 were generated by peptide immunization and screening of phage display libraries using extracellular loop 2 (ECL2) peptides of Human NTSR1 resulting in the isolation of 7C3 scFv. The unique 7C3 scFv binder was converted to full-length IgG and tested for the binding affinity to cyclic ECL2 peptides. See FIG. 1A. Binding of the 7C3 IgG to cell surface NTSR1 was measured with flow cytometry on lung cancer cell line A549 cells. 7C3 antibody displayed strong binding to A549 cells. See FIG. 1B.

Example 3: Affinity Maturation of Anti-NTSR1 Antibody

To increase the affinity of 7C3 antibody (having SEQ ID NOs: 1 and 2), variants were tested through the use of a computer model. At the basis of the model was a large repertoire of discrete antibodies and antigens having three-dimensional structures that exhibit properties similar to those of the real populations. Three variants were created, including h7C3-1 (bearing Y100H mutation in CDR H3), h7C3-2 (harboring Y100H mutation in CDR H3 and S97A mutation in CDR L3), and h7C3-3 (bearing T28A mutation in CDR H1, Y100H mutation in CDR H3, and S97A mutation in CDR L3). To investigate the activity of variants in affinity enhancement, those antibodies were subjected to FACS analysis. Among these variants, h7C3-3 revealed a lower $K_D$ value of 0.3 nM (FIG. 2) and an EC50 value of 1.1 μg/ml (Table 1), indicating that these amino acid substitutions confer affinity improvement. Table 2 shows the CDR sequences of h7C3-3.

TABLE 1

Affinity of various anti-NTSR1 antibodies after affinity maturation

| | VH | | VL | FACS binding | FACS binding | EC50[b] |
|---|---|---|---|---|---|---|
| variant | 28 | 100 | 97 | (%, 1 μg/ml[a]) | (%, 10 μg/ml[a]) | (μg/ml) |
| 7C3 | T | Y | S | 16.8 | 83.2 | 11.3 ± 2.8 |
| h7C3-1 | T | H | S | 41 | 93.1 | 7.6 ± 1.7 |
| h7C3-2 | T | H | A | 86.0 | 99.5 | 1.5 ± 0.5 |
| h7C3-3 | A | H | A | 98.7 | 100 | 1.1 ± 0.1 |

[a]Dose-dependent binding capacity of anti-NTSR1 antibody (1 μg/ml and 10 μg/ml) on A549 cells.

[b]The effective concentration (EC50) relative mean fluorescence intensity (MFI) of anti-NTSR1 antibody on A549 cells, respectively.

TABLE 2

| The CDR sequences (Kabat definition) of h7C3-3 | |
|---|---|
| Heavy chain | Light chain |
| CDR1: GYAFTSSWIH (SEQ ID NO: 4) | CDR1: RSSQSIVHSNGNTYLE (SEQ ID NO: 9) |
| CDR2: QIRPNSGNTYYNEKFKV (SEQ ID NO: 5) | CDR2: KVSNRFS (SEQ ID NO: 10) |
| CDR3: ARYHYGFDY (SEQ ID NO: 7) | CDR3: FQGAHLPWT (SEQ ID NO: 12) |

Example 4: Alanine Scanning of CDR Region of Anti-NTSR1 Antibody

To identify permissive sites in the CDR H3 that involved in antigen binding, variants were tested using experimental alanine scanning mutagenesis at 8 sites in CDR H3 of h7C3. The variants were compared in an enzyme-linked immunosorbent assay (ELISA) for their ability to bind to cyclic ECL2 peptide. R98A, Y99A, Y100A, Y101A, G102A and F103A significantly diminished the apparent affinities of h7C3 for the peptide by about 30-70%. Other substitutions had no effect on h7C3 affinity, including D104A and Y105A. Based on the result of computer modeling, replacement of Y100 by H on h7C3 binding activity was investigated. h7C3 bearing Y100H mutation exhibiting higher affinity.

Results indicated that h7C3-1 antibody (h7C3 containing Y100H mutation within the CDR H3) displayed higher affinity compared with that of parental h7C3. Variants at 9 sites in CDR L3 in h7C3-1 were tested via alanine scanning mutagenesis. Several residues significantly diminished h7C3-1 affinity, particularly F94A and W101A (by 30 to 40%), but also L99A (by 70%). Replacement of G91 by A produced a large increase in affinity of h7C3-1 for peptide. Other substitutions had no effect on h7C3-1 affinity, including G96A, S97A, H98A and P100A. To further confirm the binding of variants to cell surface NTSR1, h7C3-1 bearing G96A, S97A, H98A or P100A were subject to FACS analysis. Compared with that of h7C3-1, G96A or P100A mutation significantly diminished h7C3-1 binding affinity to cell surface NTSR1, whereas H98A slightly affects its binding to NTSR1 Surprisingly, h7C3-1 harboring S97A mutation exhibited higher affinity.

In order to identify the critical residues for antigen-antibody interaction, alanine scanning mutagenesis was carried out at 10 and 18 sites in CDR H1 and CDR H2, respectively, in h7C3-2. G26A, Y27A, W33A, I34A, H35A, Q50A, R52A and Y59A, significantly diminished the apparent affinities of h7C3-2 for the peptide by about 50% or more. Nineteen of the 28 mutants retained >80% of the h7C3-2 binding activity, including five in CDR H1 (T28A, F29A, T30A, S31A and S32A) and fourteen in CDR H2 (I51A, P53A, N54A, S55A, G56A, N57A, T58A, Y60A, N61A, E62A, K63A, F64A, K65A and V66A). h7C3-2 variants bearing T28A or N54A mutation exhibited higher binding affinity to peptide and were subjected to FACS analysis. Interestingly, h7C3-2 harboring T28A mutation in CDR H1 displayed higher affinity for NTSR1 on A549 cells.

Example 5: h7C3-3 Internalization

To examine whether h7C3-3 internalized upon binding to the cell surface, and therefore represented a candidate for cytotoxic payload conjugation, A549, H1299, HA22T or Mahlavu cells were exposed to antibodies (10 μg/ml) and analyzed by FACS. As shown in FIG. 3A, along with the extension of incubation time, the magnitude of mean fluorescence intensity (MFI) decreased gradually upon shifting the cells from 4° C. to 37° C., which represented an increasing number of h7C3-3 antibodies taken by A549 cells. Similar results were observed on H1299 cells (FIG. 3B), HA22T cells (FIG. 3C) and Mahlavu cells (FIG. 3D). These results indicated that h7C3-3 quickly and efficiently internalized in NTSR1 expressing cells.

Example 6: Characterization of h7C3-4 and h7C3-5

Figure 4:
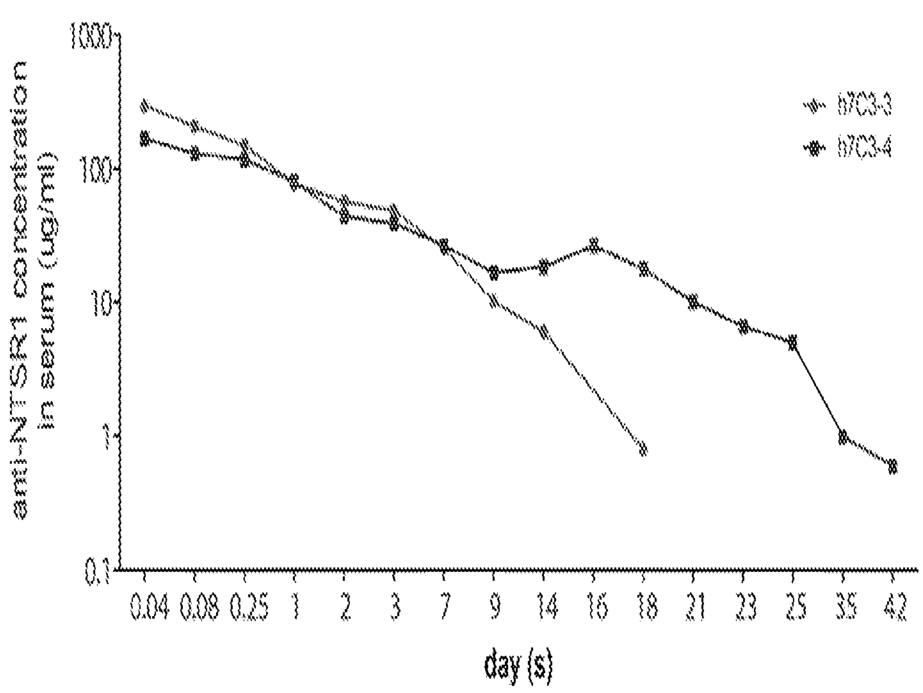
FIG. 4 includes a table and a graph showing characterization of h7C3-4 variant antibody. (A) Isoelectric points (pI) and binding affinity of h7C3-3 or h7C3-4. Binding of h7C3-3 or h7C3-4 on NTSR1 expressing A549 cells were measured with flow cytometry at a concentration of 0.5 μg/ml. (B) Pharmacokinetics of antibody in BLTW:CD1 (ICR) mice. Serum concentration of antibody relative to time profiles after single intravenous administration (10 mg/kg). Concentration of h7C3-3 or h7C3-4 antibodies in mice serum were analyzed by ELISA.

To improve the pharmacokinetics property of h7C3-3, h7C3-4 (bearing S9T and D82E mutation in the VH domain and K79T mutation in the VL domain as compared to h7C3-3) was created through the use of a computer model. As shown in FIG. 4A, h7C3-4 with lower isoelectric points (pI) values exhibited similar binding affinity as compared to h7C3-3. Additionally, h7C3-4 significantly improved clearance after saphenous vein injections compared with h7C3-3. See FIG. 4B. These results indicated that h7C3-4 has better pharmacokinetics.

An additional variant, h7C3-5, was also created. See FIG. 5, A and B. h7C3-5 exhibited a similar binding affinity to NTSR1 on A549 cells as compared to h7C3-4. See FIG. 5C.

Example 7: Characterization of Anti-NTSR1 Antibody Conjugate MMAE

Figure 6:
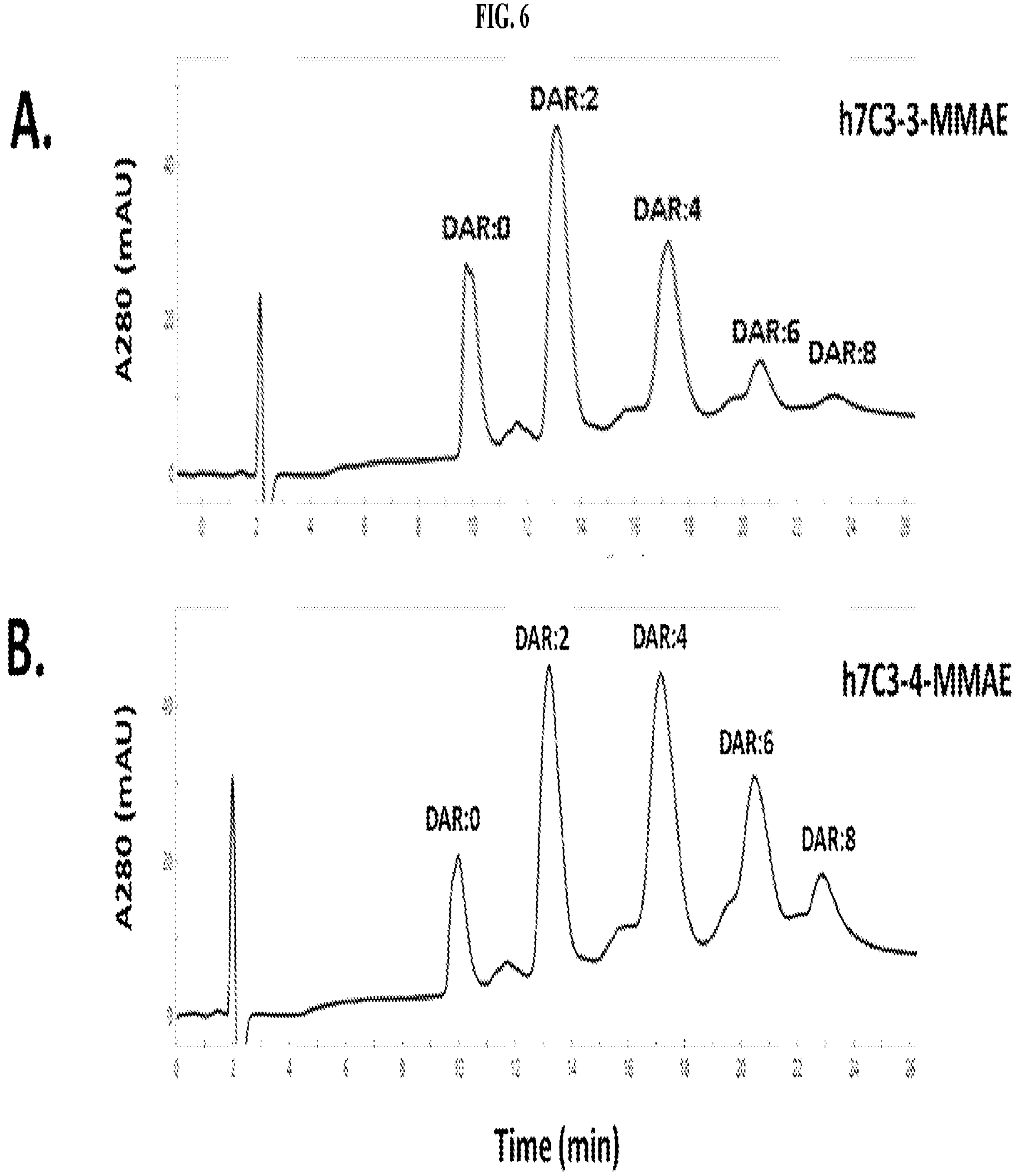
FIG. 6 is a set of graphs showing hydrophobic interaction chromatography (HIC) analysis of (A) h7C3-3-MMAE and (B) h7C3-4-MMAE conjugates. "DAR:0", "DAR:2", "DAR:4", "DAR:6" and "DAR:8 refer to the isomers of the conjugates with 0, 2, 4, 6 and 8 MMAE molecules attached per antibody, respectively.

Upon achieving high efficient production of h7C3-3 and h7C3-in Expi293 cells, conjugation of the anti-NTSR1 antibodies with the antimitotic, tubulin-inhibiting agent monomethyl auristatin E (MMAE) via a cleavable chemical linker was explored. The ADCs were prepared by partial reduction of inter-molecule disulfide bonds followed by conjugation with the thiol-reactive, maleimido-containing drug linker. The identities of these two ADCs were confirmed by HIC. HIC analysis allowed resolution of the conjunction into five major peaks corresponding to zero, two, four, six, or eight drug molecules per anti-NTSR1 antibody (FIG. 6, A and B), with average DAR around 3.8 to 4.

Example 8: Internalization Efficiency of Anti-NTSR1 Antibody-Drug Conjugates

Figure 7:
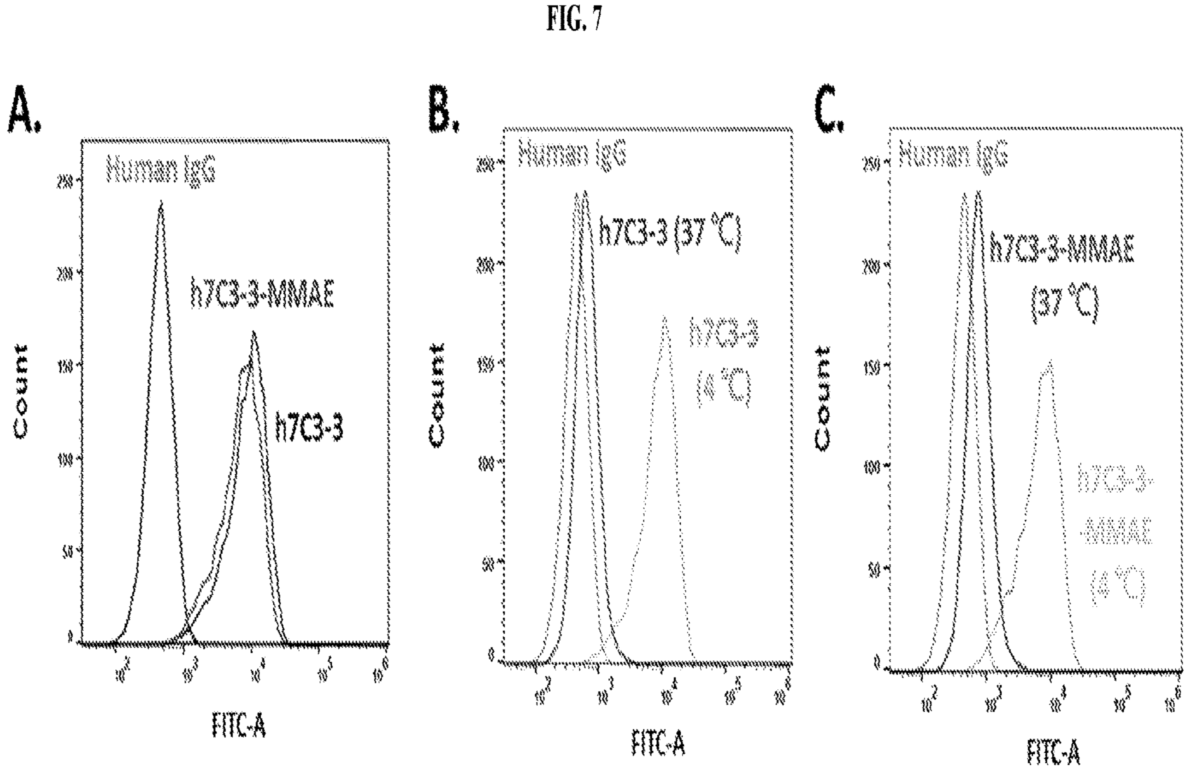
FIG. 7 is a set of graphs showing the internalization efficiency of h7C3-3 and h7C3-3-MMAE on A549 cell. (A) The binding affinity of h7C3-3 and h7C3-3-MMAE on A549 cancer cells was measured by flow cytometric after one hour incubation at 4° C. The cells distributions are to the right. (B and C) Flow cytometric analyses were applied to evaluate the internalization efficiency of h7C3-3 and h7C3-3-MMAE at a concentration of 1 μg/ml on NTSR1-expressing A549 cancer cells. Cells were incubated with antibodies on ice for 1 hour. Unbound antibodies were washed away. The experimental groups were then incubated at 37° C. for 90 minutes. After harvesting, cells were stained with FITC conjugated anti-human IgG and subjected to flow cytometry analysis. The internalization of cell distribution is to the left.

The anti-NTSR1 ADC consisted of a peptide cleavable maleimidocaproyl-valine citruline-p-aminobenzyloxycarbonyl (vc) linker introduced into the target cells and their subsequent release, usually by lysosomal proteases, is important for cytotoxic drug delivery. The internalization of h7C3-3-MMAE ADC was measured and compared with the human IgG Ab (negative control) and parental unconjugated Ab (positive control) on NTSR1-expressing NSCLC cell line A549. Both h7C3-3-MMAE and unconjugated parental Ab (h7C3-3) have binding efficiency on cell surface, the cells distributions being to the right (FIG. 7A). In order to initiate the internalization of h7C3-3-MMAE or h7C3-3, primary antibody-treated cells were suspended in 100 μL FACS buffer and incubated in a 37° C. for 90 minutes before secondary detecting Ab incubation. When the primary antibody was internalized into the cells at 37° C., the cells distributions were to the left. Both h7C3-3-MMAE and the unconjugated parental antibody (h7C3-3) internalized efficiently. See FIG. 7, B and C.

Example 9: Cytotoxic Effect of Anti-NTSR1 Antibody-Drug Conjugates

NTSR1—specific ADCs were generated by conjugation of h7C3-3, h7C3-4, and h7C3-5 with the dolastatin analogs MMAE. Auristatins are potent cytotoxic agents that induce cell death by disrupting microtubules. h7C3-3-MMAE, h7C3-4-MMAE, and h7C3-5-MMAE contain a protease-sensitive valine-citrulline dipeptide sequence designed for optimal stability in human plasma and efficient cleavage by human cathepsin B. Following internalization, lysosomal proteases metabolize both the antibody and linker to release the active drug. NTSR1-specific ADCs were conjugated with an average of 3.8-4 MMAE per antibody, a ratio that was shown to provide the optimal therapeutic index for brentuximab vedotin, polatuzumab vedotin and enfortumab vedotin.

TABLE 3

Cytotoxic effect of h7C3-3 and h7C3-3-MMAE on various NTSR1 expressing cancer cell lines

| | $IC_{50}$ (nM) | |
|---|---|---|
| Cell line | h7C3-3 | h7C3-3-MMAE |
| A549 | >500 | 40.87 ± 1.63 |
| H1299 | >500 | 95.58 ± 2.02 |
| HA22T | >500 | 36.94 ± 3.04 |
| HA22T-Luc | >500 | 39.41 ± 2.87 |
| Mahlavu | >500 | 235.65 ± 6.90 |
| PC-3 | >500 | 21.93 ± 2.04 |

Direct comparison of h7C3-3 and h7C3-3-MMAE in vitro confirmed that target binding and internalization characteristics were preserved in the ADC. See Table 3 and FIG. 8. The NTSR1-specific ADC showed excellent cytotoxicity in vitro.

Figure 9:
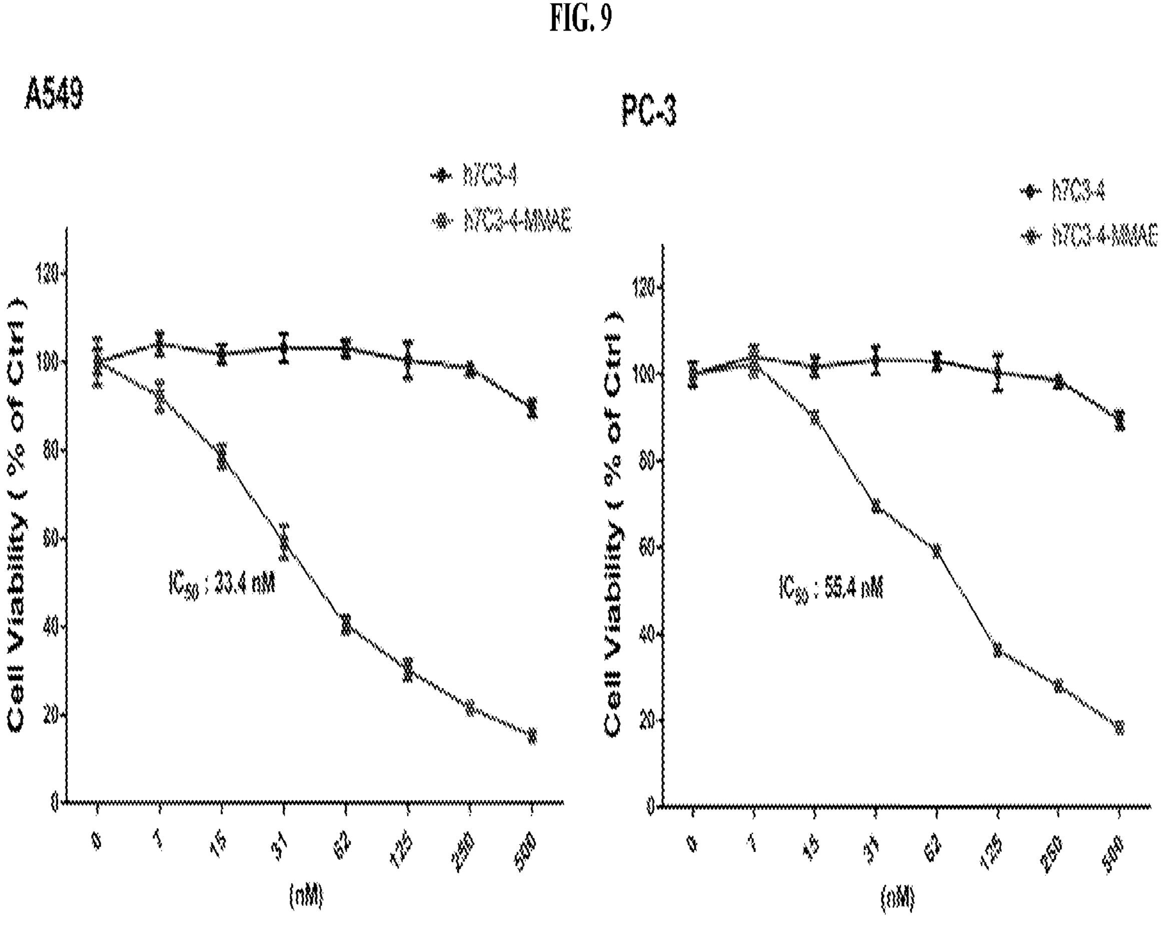
FIG. 9 includes graphs and a table showing the in vitro cytotoxic effect of h7C3-4-MMAE in various cancer cell lines.

Comparison of h7C3-4 and h7C3-4-MMAE in in vitro cytotoxicity assay also showed that the ADC exhibited target binding, internalization, and cytotoxicity. See Table 4 and FIG. 9.

h7C3-5 and h7C3-5-MMAE were compared in in vitro cytotoxicity assay. The results showed that this ADC also exhibited excellent cytotoxicity. See Table 5 and FIG. 10.

As shown in Table 6, h7C3-4-MMAE and h7C3-5-MMAE exhibited comparable in vitro cytotoxic effect in the cell lines tested.

TABLE 4

Cytotoxic effect of h7C3-4 and h7C3-4-MMAE on various NTSR1 expressing cancer cell lines

| | $IC_{50}$ (nM) | |
|---|---|---|
| Cell line | h7C3-4 | h7C3-4-MMAE |
| A549 | >500 | 33.46 ± 3.32 |
| PC-3 | >500 | 55.43 ± 5.17 |

TABLE 5

Cytotoxic effect of h7C3-5 and h7C3-5-MMAE on various NTSR1 expressing cancer cell lines

| | $IC_{50}$ (nM) | |
|---|---|---|
| Cell line | h7C3-5 | h7C3-5-MMAE |
| A549 | >500 | 33.07 ± 1.72 |
| PC-3 | >500 | 56.49 ± 7.10 |

TABLE 6

Cytotoxic effect of h7C3-4-MMAE and h7C3-5-MMAE on various NTSR1 expressing cancer cell lines

| | $IC_{50}$ (nM) | |
|---|---|---|
| Cell line | h7C3-4-MMAE | h7C3-5-MMAE |
| A549 | 33.46 ± 3.32 | 33.07 ± 1.72 |
| PC-3 | 55.43 ± 5.17 | 56.49 ± 7.10 |

Example 10: Antitumor Activity In Vivo

The in vivo effects of anti-NTSR1 ADC on target cells were evaluated in several 15 NTSR1-positive xenograft models.

Figure 10:
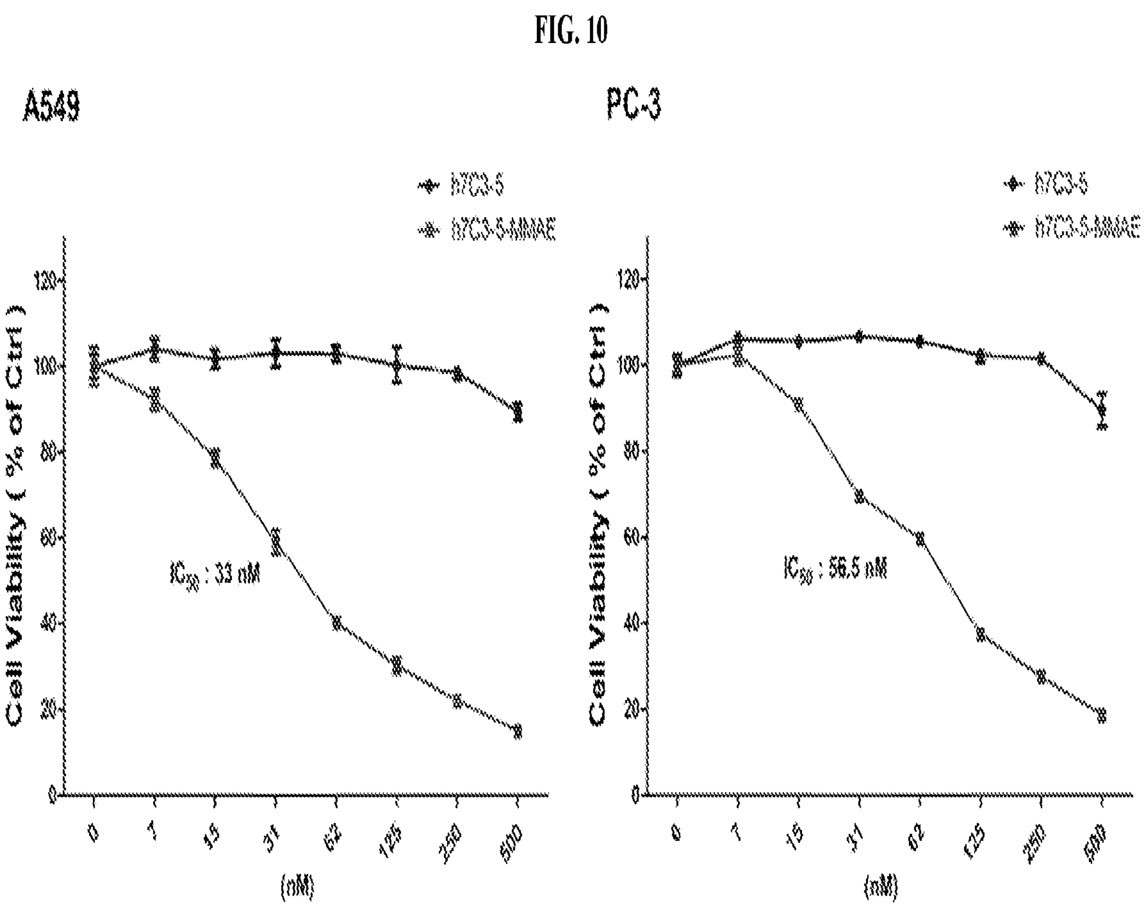
FIG. 10 includes graphs and a table showing the in vitro cytotoxic effect of h7C3-5-MMAE in various cancer cell lines.

Nude mice were subcutaneously inoculated with NTSR1-expressing cells, H1299 ($1\times10^6$ cells per mouse). When the tumors reached a volume of 200 $mm^3$, the tumor-bearing mice were grouped (n=6) and administered intravenously with human IgG (negative control), h7C3-3-MMAE, h7C3-4 and h7C3-4-MMAE, respectively, at 10 mg/Kg twice weekly for six doses. The Cisplatin (positive control) was administered intravenously at 7 mg/Kg weekly for three doses. As shown in FIG. 11A, 10 mg/kg of h7C3-4-MMAE inhibited the tumor growth more potently than the control human IgG (10 mg/kg) and Cisplatin (7 mg/kg) groups on day 18. Prolonged regression of tumor was observed in h7C3-4-MMAE treatment until 35 days compared with Cisplatin, a positive control commonly used in clinical therapeutic treatments for non-small cell lung cancer. Furthermore, 10 mg/kg of h7C3-3-MMAE showed partial inhibition of the tumor growth on day 35, indicating that h7C3-4 was internalized more efficiently than h7C3-3 in lung xenograft model.

Figure 12:
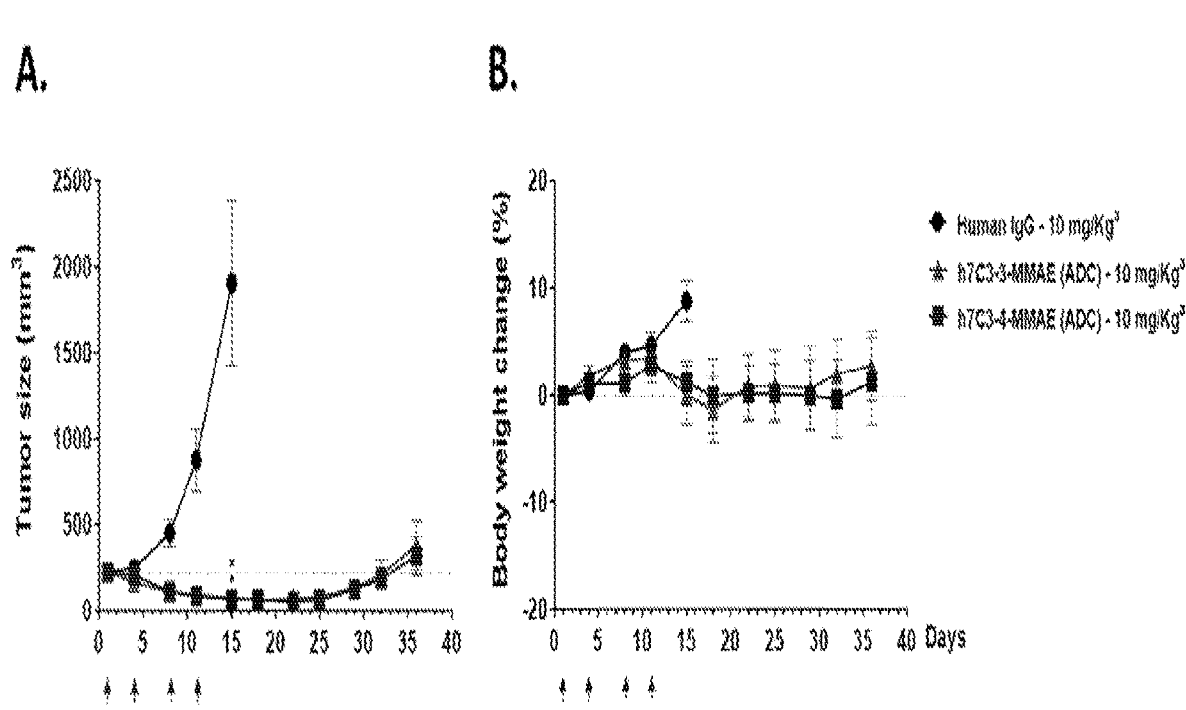
FIG. 12 is a set of graphs showing efficacies of anti-NTSR1 h7C3-3-MMAE and h7C3-4-MMAE at a dose of 10 mg/kg in the HA22T-Luc liver tumor xenografts model. (A) Antitumor efficacies of h7C3-3-MMAE and h7C3-4-MMAE are shown with changes in tumor volumes. (B) Both groups did not show body weight loss.

To compare the anti-tumor efficacies of h7C3-3-MMAE and h7C3-4 MMAE, an experiment was performed with $5\times10^6$ HA22T-luc liver cancer cells inoculated subcutaneously to SCID mice. Tumor-bearing mice were divided into 3 groups (n=8). When the tumors reached a volume of 200 $mm^3$, 10 mg/Kg of human IgG, h7C3-3-MMAE and h7C3-4 MMAE were administered intravenously, respectively, twice weekly for four doses. Both h7C3-3-MMAE and h7C3-4 MMAE showed tumor regression on day 15 (FIG. 12A), and prolonged regression of tumor were observed in both ADC treatments until 36 days.

Figure 13:
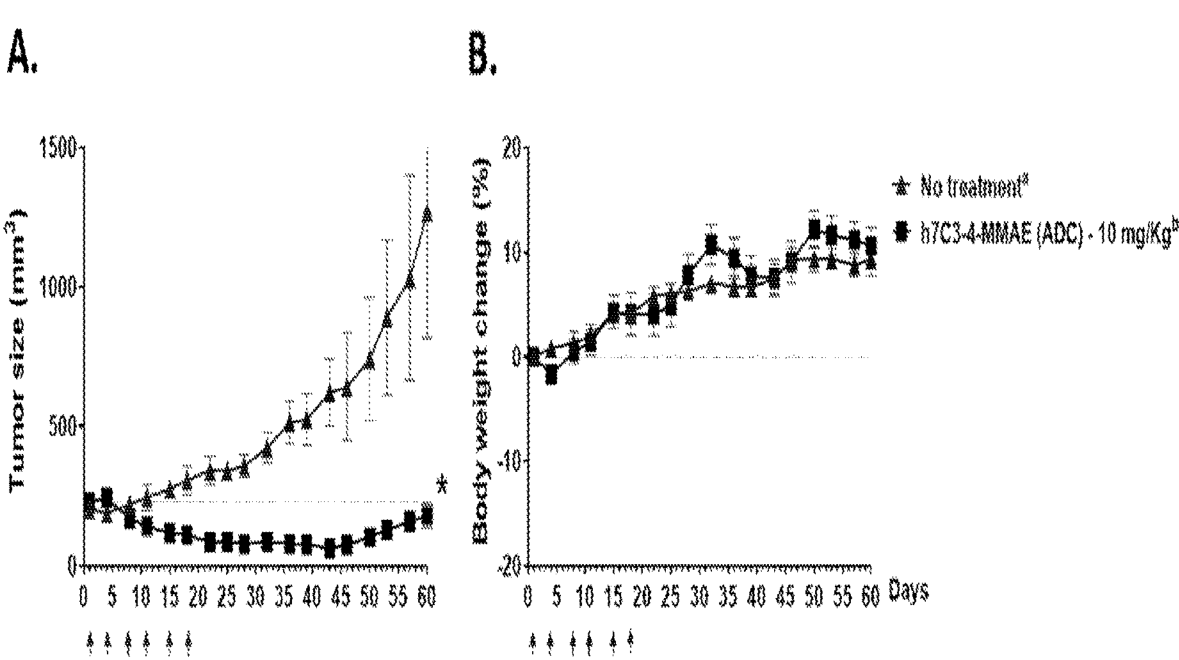
FIG. 13 is a set of graphs showing efficacies of anti-NTSR1 h7C3-4-MMAE at a dose of 10 mg/kg in the PC3 prostate tumor xenograft model. (A) Antitumor efficacy of h7C3 MMAE is shown with changes in tumor volumes. (B) The treatment did not cause body weight loss.

Additional experiment was performed with the PC3 prostate cancer cell line ($1\times10^6$ cells) xenograft using h7C3-4-MMAE treatment (FIG. 13A). When the tumors reached a volume of 200 $mm^3$, the tumor-bearing mice were divided into no treatment (n=5) and h7C3-4-MMAE (n=8) groups. 10 mg/kg of h7C3-4-MMAE was administered intravenously twice weekly for six doses. h7C3-4-MMAE was also shown to be highly efficacious in PC3 prostate cancer type. The prolonged regression of tumor was observed in h7C3-

4-MMAE treatment until day 60. Tumor regression with dosing treatment did not induce any abnormalities in the general physiological conditions or body weight changes of the mice (FIG. 8B, 9B, 10B), indicating that h7C3-3-MMAE or h7C3-4-MMAE are potent agents for the treatment of NTSR1-positive malignancies.

Example 11: Immunohistochemistry Staining

Figure 14:
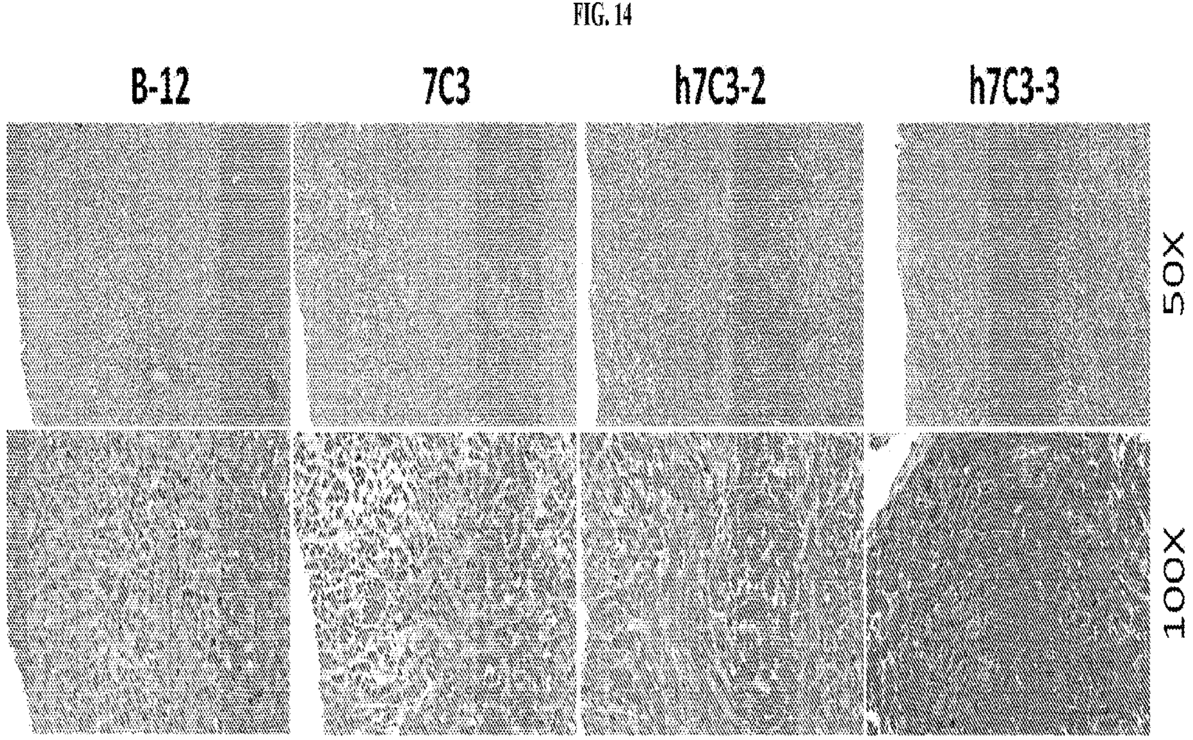
FIG. 14 is a set of images showing immunohistochemical staining of xenograft PC-3 prostate cancer tissue with 2 μg/ml B-12, 7C3, h7C3-2, or h7C3-3 antibodies. Solid tumors were excised from PC-3 xenograft mice without treatment, followed by immunohistochemistry staining using antibodies specific for NTSR1. Images were taken at 50×and 100× magnification.

To evaluate NTSR1 expression on prostate cancer cells, PC-3 xenograft tumor tissues were subjected to NTSR1 immunohistochemistry staining with 2 μg/ml B-12 (anti-NTSR1-B12; SC-376958, Santa Cruz Biotechnology), 7C3, h7C3-2, or h7C3-3 antibodies. See FIG. 14 Immunohistochemistry staining has shown strong NTR1 expression on PC-3 xenograft tumor tissues. Among these antibodies, the staining of h7C3-3 was clustered and more intense, suggesting that h7C3-3 is suitable for immunohistochemistry staining.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An isolated antibody comprising:

(a) a heavy chain CDR1 comprising the sequence of SEQ ID NO: 3, a heavy chain CDR2 comprising the sequence of SEQ ID NO: 5, a heavy chain CDR3 comprising the sequence of SEQ ID NO: 7 or SEQ ID NO: 8, a light chain CDR1 comprising the sequence of SEQ ID NO: 9, a light chain CDR2 comprising the sequence of SEQ ID NO: 10, and a light chain CDR3 comprising the sequence of SEQ ID NO: 11 or SEQ ID NO: 12;

(b) a heavy chain CDR1 comprising the sequence of SEQ ID NO: 4, a heavy chain CDR2 comprising the sequence of SEQ ID NO: 5, a heavy chain CDR3 comprising the sequence of SEQ ID NO: 6 or SEQ ID NO: 8, a light chain CDR1 comprising the sequence of SEQ ID NO: 9, a light chain CDR2 comprising the sequence of SEQ ID NO: 10, and a light chain CDR3 comprising the sequence of SEQ ID NO: 11 or SEQ ID NO: 12;

(c) a heavy chain CDR1 comprising the sequence of SEQ ID NO: 3, a heavy chain CDR2 comprising the sequence of SEQ ID NO: 5, a heavy chain CDR3 comprising the sequence of SEQ ID NO: 6, a light chain CDR1 comprising the sequence of SEQ ID NO: 9, a light chain CDR2 comprising the sequence of SEQ ID NO: 10, and a light chain CDR3 comprising the sequence of SEQ ID NO: 12;

(d) a $V_H$ sequence comprising the sequence of SEQ ID NO: 13 and a $V_L$ sequence comprising the sequence of SEQ ID NO: 14; or (e) a $V_H$ sequence comprising the sequence of SEQ ID NO: 15 and a $V_L$ sequence comprising the sequence of SEQ ID NO: 16;

wherein the antibody binds specifically to human neurotensin receptor 1 (hNTSR1).

2. The isolated antibody of claim 1, wherein the antibody includes:

a heavy chain CDR1 comprising the sequence of SEQ ID NO: 4, a heavy chain CDR2 comprising the sequence of SEQ ID NO: 5, a heavy chain CDR3 comprising the sequence of SEQ ID NO: 8, a light chain CDR1 comprising the sequence of SEQ ID NO: 9, a light chain CDR2 comprising the sequence of SEQ ID NO: 10, and a light chain CDR3 comprising the sequence of SEQ ID NO: 12.

3. The isolated antibody of claim 1, wherein the antibody includes:

a heavy chain CDR1 comprising the sequence of SEQ ID NO: 4, a heavy chain CDR2 comprising the sequence of SEQ ID NO: 5, a heavy chain CDR3 comprising the sequence of SEQ ID NO: 6, a light chain CDR1 comprising the sequence of SEQ ID NO: 9, a light chain CDR2 comprising the sequence of SEQ ID NO: 10, and a light chain CDR3 comprising the sequence of SEQ ID NO: 12.

4. The isolated antibody of claim 1, wherein the antibody includes:

a heavy chain CDR1 comprising the sequence of SEQ ID NO: 3, a heavy chain CDR2 comprising the sequence of SEQ ID NO: 5, a heavy chain CDR3 comprising the sequence of SEQ ID NO: 7 or SEQ ID NO: 8, a light chain CDR1 comprising the sequence of SEQ ID NO: 9, a light chain CDR2 comprising the sequence of SEQ ID NO: 10, and a light chain CDR3 comprising the sequence of SEQ ID NO: 11.

5. The isolated antibody of claim 1, wherein the antibody includes:

a heavy chain CDR1 comprising the sequence of SEQ ID NO: 3, a heavy chain CDR2 comprising the sequence of SEQ ID NO: 5, a heavy chain CDR3 comprising the sequence of SEQ ID NO: 7 or SEQ ID NO: 8, a light chain CDR1 comprising the sequence of SEQ ID NO: 9, a light chain CDR2 comprising the sequence of SEQ ID NO: 10, and a light chain CDR3 comprising the sequence of SEQ ID NO: 12.

6. The isolated antibody of claim 1, wherein the antibody includes:

a heavy chain CDR1 comprising the sequence of SEQ ID NO: 3, a heavy chain CDR2 comprising the sequence of SEQ ID NO: 5, a heavy chain CDR3 comprising the sequence of SEQ ID NO: 6, a light chain CDR1 comprising the sequence of SEQ ID NO: 9, a light chain CDR2 comprising the sequence of SEQ ID NO: 10, and a light chain CDR3 comprising the sequence of SEQ ID NO: 12.

7. The isolated antibody of claim 1, wherein the antibody includes a $V_H$ sequence comprising the sequence of SEQ ID NO: 13; and a $V_L$ sequence comprising the sequence of SEQ ID NO: 14.

8. The isolated antibody of claim 1, wherein the antibody includes a $V_H$ sequence comprising the sequence of SEQ ID NO: 15; and a $V_L$ sequence comprising the sequence of SEQ ID NO: 16.

9. The isolated antibody of claim 1, wherein the antibody is a recombinant antibody, a monoclonal antibody, a chimeric antibody, a humanized antibody, an IgG1 antibody, or an antibody fragment comprising an antigen-binding site.

10. A pharmaceutical composition, comprising the isolated antibody of claim 1 and a pharmaceutical carrier.

11. An antibody conjugate, comprising:

the isolated antibody of claim 1; and a non-antibody molecule.

12. The antibody conjugate of claim 11, wherein the non-antibody molecule is a polypeptide, a polymer, an oligosaccharide, a lipid, a glycolipid, a solid support, a small molecule drug, a biotin, a nucleic acid molecule, a carrier protein, or a detectable label.

13. The antibody conjugate of claim 12, wherein the conjugate is an antibody-drug conjugate.

14. The antibody conjugate of claim 13, wherein the non-antibody molecule is a cancer drug for treating a tumor that expresses hNTSR1.

15. The antibody conjugate of claim 14, wherein the tumor is a mesothelioma, a lung tumor, a breast tumor, a head and neck squamous carcinoma, a colon tumor, a pancreatic tumor, a prostate tumor, or a liver carcinoma.

16. The antibody conjugate of claim 15, wherein the cancer drug is monomethyl auristin E (MMAE).

17. A pharmaceutical composition, comprising the antibody-drug conjugate of claim 14 and a pharmaceutical carrier.

18. A method of treating a tumor in a subject, comprising:

administering the pharmaceutical composition of claim 17 to a subject in need thereof, wherein the tumor expresses hNTSR1.

19. The method of claim 18, wherein the tumor is a mesothelioma, lung tumor, breast tumor, head and neck squamous carcinoma, colon tumor, pancreatic tumor, prostate tumor, or liver carcinoma.

20. A method of detecting hNTSR1, comprising:

contacting a sample, tissue or cell with the antibody of claim 1 or the antibody conjugate of claim 12; and determining binding of the antibody or antibody conjugate to a target in the sample, or to the tissue or cell.

21. The method of claim 20, wherein the antibody conjugate includes a detectable label.

* * * * *

SEQUENCE LISTING

```
<160> NUMBER OF SEQ ID NOS: 16

<210> SEQ ID NO 1
<211> LENGTH: 116
<212> TYPE: PRT
<213> ORGANISM: Artificial Sequence
<220> FEATURE:
<223> OTHER INFORMATION: VH SEQUENCE

<400> SEQUENCE: 1

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Ala Lys Gln Arg Pro Gly Gln Gly Leu Glu Trp Ile
        35                  40                  45

Gly Gln Ile Arg Pro Asn Ser Gly Asn Thr Tyr Tyr Asn Glu Lys Phe
    50                  55                  60

Lys Val Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Tyr Tyr Tyr Gly Phe Asp Tyr Trp Gly Gln Gly Thr Leu Val
            100                 105                 110

Thr Val Ser Ser
        115


<210> SEQ ID NO 2
<211> LENGTH: 113
<212> TYPE: PRT
<213> ORGANISM: Artificial Sequence
<220> FEATURE:
<223> OTHER INFORMATION: VL SEQUENCE

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Trp Thr Phe Gly Gly Gly Thr Lys Leu Glu Ile Lys
            100                 105                 110

Arg


<210> SEQ ID NO 3
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 3

Gly Tyr Thr Phe Thr Ser Ser Trp Ile His
1               5                   10


<210> SEQ ID NO 4
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 4

Gly Tyr Ala Phe Thr Ser Ser Trp Ile His
1               5                   10


<210> SEQ ID NO 5
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 5

Gln Ile Arg Pro Asn Ser Gly Asn Thr Tyr Tyr Asn Glu Lys Phe Lys
1               5                   10                  15

Val


<210> SEQ ID NO 6
<211> LENGTH: 9
<212> TYPE: PRT
<213> ORGANISM: Artificial Sequence
<220> FEATURE:
<223> OTHER INFORMATION: heavy chain CDR3

<400> SEQUENCE: 6

Ala Arg Tyr Tyr Tyr Gly Phe Asp Tyr
1               5


<210> SEQ ID NO 7
<211> LENGTH: 9
<212> TYPE: PRT
<213> ORGANISM: Artificial Sequence
<220> FEATURE:
<223> OTHER INFORMATION: heavy chain CDR3

<400> SEQUENCE: 7

Ala Arg Tyr His Tyr Gly Phe Asp Tyr
```

1 5

<210> SEQ ID NO 8
<211> LENGTH: 9
<212> TYPE: PRT
<213> ORGANISM: Artificial Sequence
<220> FEATURE:
<223> OTHER INFORMATION: heavy chain CDR3

<400> SEQUENCE: 8

Ala Arg Tyr Arg Tyr Gly Phe Asp Tyr
1 5

<210> SEQ ID NO 9
<211> LENGTH: 16
<212> TYPE: PRT
<213> ORGANISM: Artificial Sequence
<220> FEATURE:
<223> OTHER INFORMATION: light chain CDR1

<400> SEQUENCE: 9

Arg Ser Ser Gln Ser Ile Val His Ser Asn Gly Asn Thr Tyr Leu Glu
1 5 10 15

<210> SEQ ID NO 10
<211> LENGTH: 7
<212> TYPE: PRT
<213> ORGANISM: Artificial Sequence
<220> FEATURE:
<223> OTHER INFORMATION: light chain CDR2

<400> SEQUENCE: 10

Lys Val Ser Asn Arg Phe Ser
1 5

<210> SEQ ID NO 11
<211> LENGTH: 9
<212> TYPE: PRT
<213> ORGANISM: Artificial Sequence
<220> FEATURE:
<223> OTHER INFORMATION: light chain CDR3

<400> SEQUENCE: 11

Phe Gln Gly Ser His Leu Pro Trp Thr
1 5

<210> SEQ ID NO 12
<211> LENGTH: 9
<212> TYPE: PRT
<213> ORGANISM: Artificial Sequence
<220> FEATURE:
<223> OTHER INFORMATION: light chain CDR3

<400> SEQUENCE: 12

Phe Gln Gly Ala His Leu Pro Trp Thr
1 5

<210> SEQ ID NO 13
<211> LENGTH: 116
<212> TYPE: PRT
<213> ORGANISM: Artificial Sequence
<220> FEATURE:
<223> OTHER INFORMATION: VH SEQUENCE

<400> SEQUENCE: 13

Gln Val Gln Leu Gln Gln Pro Gly Thr Val Leu Val Arg Pro Gly Ala
1 5 10 15

```
Ser Val Lys Leu Ser Cys Lys Ala Ser Gly Tyr Ala Phe Thr Ser Ser
            20                  25                  30

Trp Ile His Trp Ala Lys Gln Arg Pro Gly Gln Gly Leu Glu Trp Ile
        35                  40                  45

Gly Gln Ile Arg Pro Asn Ser Gly Asn Thr Tyr Tyr Asn Glu Lys Phe
    50                  55                  60

Lys Val Lys Ala Thr Leu Thr Val Asp Thr Ser Ser Ser Thr Ala Tyr
65                  70                  75                  80

Val Glu Leu Ser Ser Leu Thr Ser Glu Asp Ser Ala Val Tyr Tyr Cys
                85                  90                  95

Ala Arg Tyr His Tyr Gly Phe Asp Tyr Trp Gly Gln Gly Thr Leu Val
            100                 105                 110

Thr Val Ser Ser
        115


<210> SEQ ID NO 14
<211> LENGTH: 113
<212> TYPE: PRT
<213> ORGANISM: Artificial Sequence
<220> FEATURE:
<223> OTHER INFORMATION: VL SEQUENCE

<400> SEQUENCE: 14

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Val Tyr Tyr Cys Phe Gln Gly
                85                  90                  95

Ala His Leu Pro Trp Thr Phe Gly Gly Gly Thr Lys Leu Glu Ile Lys
            100                 105                 110

Arg


<210> SEQ ID NO 15
<211> LENGTH: 116
<212> TYPE: PRT
<213> ORGANISM: Artificial Sequence
<220> FEATURE:
<223> OTHER INFORMATION: VH SEQUENCE

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Ser
            20                  25                  30

Trp Ile His Trp Val Arg Gln Ala Pro Gly Gln Arg Leu Glu Trp Met
        35                  40                  45

Gly Gln Ile Arg Pro Asn Ser Gly Asn Thr Tyr Tyr Asn Glu Lys Phe
    50                  55                  60

Lys Val Arg Val Thr Ile Thr Arg Asp Thr Ser Ala Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Ala Arg Tyr His Tyr Gly Phe Asp Tyr Trp Gly Gln Gly Thr Leu Val
            100                 105                 110

Thr Val Ser Ser
        115


<210> SEQ ID NO 16
<211> LENGTH: 113
<212> TYPE: PRT
<213> ORGANISM: Artificial Sequence
<220> FEATURE:
<223> OTHER INFORMATION: VL SEQUENCE

<400> SEQUENCE: 16

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ala His Leu Pro Trp Thr Phe Gly Gly Gly Thr Lys Val Glu Ile Lys
            100                 105                 110

Arg
```